(12) United States Patent
Arai et al.

(10) Patent No.: US 7,737,182 B2
(45) Date of Patent: *Jun. 15, 2010

(54) PHARMACEUTICALS FOR XEROSIS

(75) Inventors: Iwao Arai, Tokyo (JP); Nobuko Futaki, Tokyo (JP); Yuki Hashimoto, Tokyo (JP); Masanori Sugimoto, Tokyo (JP)

(73) Assignees: Taisho Pharmaceutical Co., Ltd., Tokyo (JP); Fumie Sato, Kanagawa (JP)

( * ) Notice: Subject to any disclaimer, the term of this patent is extended or adjusted under 35 U.S.C. 154(b) by 551 days.

This patent is subject to a terminal disclaimer.

(21) Appl. No.: 11/049,641

(22) Filed: Feb. 4, 2005

(65) Prior Publication Data

US 2005/0192357 A1 Sep. 1, 2005

Related U.S. Application Data

(63) Continuation-in-part of application No. 10/493,693, filed as application No. PCT/JP03/10051 on Aug. 7, 2001.

(30) Foreign Application Priority Data

Aug. 9, 2002 (JP) .............. 2002/234011
Feb. 6, 2004 (JP) .............. 2004/031286

(51) Int. Cl.
*A01N 53/00* (2006.01)
*C07C 59/00* (2006.01)
*C07C 69/74* (2006.01)

(52) U.S. Cl. .............. 514/571; 514/887; 514/861; 554/214; 560/121; 560/122

(58) Field of Classification Search .............. 514/573, 514/887, 861; 554/214; 560/122, 121
See application file for complete search history.

(56) References Cited

U.S. PATENT DOCUMENTS

| 4,454,339 | A |   | 6/1984  | Skuballa et al. |
| 4,699,920 | A |   | 10/1987 | Skuballa et al. |
| 4,789,685 | A |   | 12/1988 | Skuballa et al. |
| 4,870,104 | A |   | 9/1989  | Vorbruggen et al. |
| 4,983,629 | A |   | 1/1991  | Vorbruggen et al. |
| 5,059,622 | A | * | 10/1991 | Sears ............... 514/549 |
| 5,491,254 | A | * | 2/1996  | Sato et al. ........ 560/121 |

(Continued)

FOREIGN PATENT DOCUMENTS

EP 0 069 696 A2 1/1983

(Continued)

OTHER PUBLICATIONS

Hellhammer et al., Psychother. Psychosom, 2001, 7, 6-16.*

(Continued)

*Primary Examiner*—Johann R Richter
*Assistant Examiner*—Abigail Fisher
(74) *Attorney, Agent, or Firm*—Sughrue Mion, PLLC

(57) ABSTRACT

A method for or treating xerosis by applying a prostaglandin D receptor selective agonist to a mammal.

5 Claims, 10 Drawing Sheets

U.S. PATENT DOCUMENTS

| | | | |
|---|---|---|---|
| 5,545,666 A * | 8/1996 | Sato et al. ............... | 514/530 |
| 5,591,446 A | 1/1997 | Melnik et al. | |
| 5,599,838 A * | 2/1997 | Sato et al. ............... | 514/530 |
| 5,807,892 A | 9/1998 | Klimko et al. | |
| 5,852,050 A | 12/1998 | Melnik et al. | |
| 5,891,910 A | 4/1999 | Buchmann et al. | |
| 6,225,347 B1 | 5/2001 | Buchmann et al. | |
| 6,329,539 B1 * | 12/2001 | Sato et al. ............... | 554/214 |
| 6,395,786 B1 * | 5/2002 | Sato et al. ............... | 514/573 |
| 6,506,789 B2 | 1/2003 | Sato et al. | |
| 6,617,353 B1 * | 9/2003 | Ito et al. ............... | 514/557 |
| 6,635,678 B1 | 10/2003 | Kamm et al. | |
| 6,740,772 B1 | 5/2004 | Sato et al. | |
| 2004/0266880 A1 | 12/2004 | Sato et al. | |
| 2005/0192357 A1 | 9/2005 | Arai et al. | |

FOREIGN PATENT DOCUMENTS

| | | |
|---|---|---|
| EP | 652211 A1 | 5/1995 |
| EP | 666256 A1 | 8/1995 |
| EP | 737676 A1 | 10/1996 |
| EP | 860430 A2 | 8/1998 |
| EP | 1 084 711 A1 | 3/2001 |
| EP | 1082961 A1 | 3/2001 |
| EP | 1083168 A1 | 3/2001 |
| EP | 1097922 A1 | 5/2001 |
| EP | 1170594 A2 | 1/2002 |
| EP | 1211242 A1 | 6/2002 |
| EP | 1 245 562 A1 | 10/2002 |
| EP | 0 312 601 A1 | 5/2003 |
| EP | 1 314 719 A1 | 5/2003 |
| EP | 1477170 A1 | 11/2004 |
| JP | 7-242622 A | 9/1995 |
| JP | 07-242622 A | 9/1995 |
| JP | 7-285929 A | 10/1995 |
| JP | 07-285929 A | 10/1995 |
| JP | 09-71539 A | 3/1997 |
| JP | 09-169638 A | 6/1997 |
| JP | 09-286775 A | 11/1997 |
| JP | 9-286775 A | 11/1997 |
| JP | 10-316564 A | 12/1998 |
| JP | 11-80031 A | 3/1999 |
| JP | 11-199478 | 7/1999 |
| JP | 2000-273083 A | 10/2000 |
| JP | 2001-089443 A | 4/2001 |
| JP | 2001-122786 A | 5/2001 |
| JP | 2001-151749 A | 6/2001 |
| JP | 2001-220355 A | 8/2001 |
| WO | WO 85/00367 A1 | 1/1985 |
| WO | WO 85/02841 A1 | 7/1985 |
| WO | WO 89/00559 A1 | 1/1989 |
| WO | WO 93/06831 A1 | 4/1993 |
| WO | WO 96/16935 A1 | 6/1996 |
| WO | WO 97/45114 A1 | 12/1997 |
| WO | WO 98/27971 A1 | 7/1998 |
| WO | 99/61029 A1 | 2/1999 |
| WO | 99/61419 A1 | 2/1999 |
| WO | WO 99/25358 A1 | 5/1999 |
| WO | WO 99/62555 A1 | 12/1999 |
| WO | WO 00/32190 A1 | 6/2000 |
| WO | WO 01/19790 * | 3/2001 |
| WO | WO 01/19814 A2 | 3/2001 |
| WO | WO 01/49661 A1 | 7/2001 |
| WO | WO 02/16311 A1 | 2/2002 |
| WO | WO 02/20462 A | 3/2002 |
| WO | WO 02/045718 A1 | 6/2002 |
| WO | WO 03/070252 A1 | 8/2003 |

OTHER PUBLICATIONS

Grant et al., Advanced Drug Delivery Reviews, 2001, 48, 3-26.*
Xu et al., J. Invest Dermatol., 2001, 117, 977-983.*
Willoughby et al., Lancet, 2000, 255, 646-648.*
Merck Manual (http://www.merck.com/mmhe/sec18/ch203/ch203b.html#sb203_1, obtained online on Apr. 17, 2009).*
Pons-Guiraud, JEADV, 2007, 21 (Suppl. 2) 1-4.*
Angeli, V., et al., Role of the Parasite-derived Prostaglandin $D_2$ in the Inhibition of Epidermal Langerhans Cell Migration during Schistosomiasis Infection, J. Ex. Med. vol. 193, No. 10, May 21, 2001, pp. 1135-1147.
Amendment Under 37 C.F.R. § 1.116 filed Apr. 15, 2008 in U.S. Appl. No. 10/492,948.
The Merck Manual, www.merck.com/mmhe/sec18/ch203/ch203c.html, 2006.
Merriam-Webster Online Dictionary, www.merriam-webster.com/dictionary/preventing, 2005.
Non-Final Office Action dated Dec. 27, 2007 in U.S. Appl. No. 10/493,693.
Final Office Action dated Jan. 15, 2008 in U.S. Appl. No. 10/492,948.
Rosanna Marsella et al., "The ACVD task force on canine atopic dermatitis (XXII): nonsteroidal anti-inflammatory pharmacotherapy", Veterinary Immunology and Immunopathology, Sep. 20, 2001, vol. 81, No. 3-4, pp. 331-345.
Olivry, T. et al., "Treatment of canine atopic dermatitis with misoprostol, a prostaglandin E1 analogue: An open study", Database EMBASE [Online] XP002440431, 1997.
Lawrence S. Chan et al., "Expression of Interleukin-4 in the Epidermis of Transgenic Mice Results in a Pruritic Inflammatory Skin Disease: An Experimental Animal Model to Study Atopic Dermatitis", J. Invest. Dermatol., 2001, 117 pp. 977-983.
Angelika Buske-Kirschbaum et al., "Pyschobiological Aspects of Atopic Dermatitis: An Overview", Psychotherapy and Psychosomatics, 2001:70:6-16.
Sudha R. Vippagunta et al., "Crystalline Solids", Advanced Drug Delivery Reviews, (2001), 48, 3-26.
Non-Final Office Action dated Jul. 24, 2007 in U.S. Appl. No. 10/492,948.
Amendment Under 37 C.F.R. §1.111 filed Oct. 24, 2007 in U.S. Appl. No. 10/492,948.
Non-Final Office Action dated May 5, 2208 in U.S. Appl. No. 10/492,498.
Amendment Under 37 C.F.R. § 1.111 filed May 27, 2008 in U.S. Appl. No. 10/493,693.
Final Office Action dated Dec. 16, 2008 in U.S. Appl. No. 10/492,948.
Amendment Under 37 C.F.R. § 1.111, filed Jan. 21, 2009 in U.S. Appl. No. 10/493,693.
Non-Final Office Action dated Aug. 18, 2008, in U.S. Appl. No. 10/493,693.
Amendment Under 37 CFR 1.111, filed Oct. 6, 2008, in U.S. Appl. No. 10/492,948.
Amendment under 37 CFR 1.111 with attachment (Cell, vol. 83, 803-812 [1995]), an executed Rule 132 Declaration of N. Nagahata dated Oct. 27, 2009, and an executed Rule 132 Declaration of I. Arai dated Nov. 4, 2009, in U.S. Appl. No. 10/493,693, as filed on Nov. 9, 2009.
Examiner's Interview Summary dated Nov. 10, 2009, issued in U.S. Appl. No. 10/493,693.
Statement of Substance of Interview as filed in U.S. Appl. No. 10/493,693 on Nov. 24, 2009.
Mark Abramovitz, et al., 'The Utilization of Recombinant Prostanoid Receptors to Determine the Affinities and Selectivities of Prostaglandins and Related Analogs.
Derek A. Willoughby, et al., "COX-1, COX-2, and COX-3 and the furture treatment of chronic inflammatory disease", The Lancet, vol. 355, pp. 646-648, Feb. 19, 2000.
Non-Final Office Action dated May 14, 2009, in U.S. Appl. No. 10/493,693.

* cited by examiner

PHARMACEUTICALS FOR XEROSIS

The subject application is a continuation in-part application of U.S. application Ser. No. 10/493,693 filed on Apr. 27, 2004, which is a 371 of PCT.JP03/10051 filed on Aug. 7, 2003.

TECHNICAL FIELD

This invention relates to methods and pharmaceutical preparations for preventing or treating pruritic symptoms (the pharmaceutical preparations are hereunder sometimes referred to as antipruritics), in particular, to antipruritic methods and antipruritics effective in eliminating the itch sensation due to atopic symptoms. More particularly, the invention relates to methods and pharmaceutical preparations for preventing or treating xerosis (the pharmaceutical preparations are hereunder sometimes referred to as pharmaceutical preparations against xerosis), and even more particularly to methods and pharmaceutical preparations effective in eliminating skin damage due to diminished water content of the stratum corneum, decreased lipid between horny cells, etc.

BACKGROUND ART

Recent years have seen a rapid increase in the number of patients with pruritic symptoms as from atopic dermatitis and atopic conjunctivitis. Also increasing is the number of patients with chronic dermatoses such as xerosis due to excessive dryness caused by diminished lipid between horny cells of the skin and lowered water content of the stratum corneum, typically associated with aging. These diseases are accompanied by an intense itch sensation of obscure etiology and are aggravated by the resulting itch-evoked scratching behavior, possibly inducing inflammations in mucous membranes or skin. Therefore, eliminating an itch sensation, particularly doing so while maintaining the normal water content of the stratum corneum, is crucial to the elimination of those symptoms.

Pharmaceutical preparations conventionally used to treat those cases of chronic dermatitis include steroids for external application, antihistamines, antiallergics and humectants. However, the use of steroids is restricted for the strong side effects they may cause, and no completely satisfactory therapeutic efficacy has been obtained from antihistamines, antiallergics, humectants, etc. In addition, diseases that are ameliorated temporarily in symptoms by those drugs will occasionally recur, showing inadequacy in their therapeutic efficacy.

Heretofore, antipruritics have been assessed by administering histamine, serotonin and other pruritogens into the skin of animals and measuring their itch-evoked scratching behavior. However, it was recently reported that the manifestation of an itch due to pruritic symptoms as in atopic dermatitis is not simply the reaction caused by histamine, etc. that are released from mast cells (J. Dermatological Science 25, 20-28, 2001). What is more, on account of unknown etiology for pruritic symptoms from excessive dryness of the skin, no reliable method has been established for assessing the therapeutics available today.

Therefore, it is desired to unravel the mechanism of action in the manifestation of itch for the purpose of preventing and treating pruritic symptoms as in atopic dermatitis, in particular, those from excessive dryness of the skin, and to develop antipruritics that depend on the new mechanism of action.

Prostaglandins have been considered to be a prurigenic component (J. Am. Acad. Dermatol. 47, 28-32, 2002) but it was recently reported that a prostaglandin receptor agonist is useful as an antipruritic agent against the itch from atopic dermatitis (see WO03/070252). However, many of the substances that act on prostaglandin receptors in general often act not only on a specific receptor but also on other receptors. Therefore, if they act not only on the receptor which should develop the intended pharmaceutical efficacy but also on other receptors, there is the risk of an unwanted physiological reaction of manifesting itself as a side effect or reduced action. For example, prostaglandin D2 acts as an agonist not only on the prostaglandin receptors but also on a thromboxane (TP) receptor and it has the possibility of inducing potent vasoconstriction and platelet aggregation which are TP receptor agonistic actions (The Journal of Pharmacology And Experimental Therapeutics (2003), 305, 347-352, Br. J. Pharmacol. (1989), 96, 688-692). In the presence of such side effects, the utility of a particular prostaglandin receptor agonist as an antipruritic agent is limited.

Therefore, the development of an antipruritic agent having less of the unwanted physiological reactions is desired.

DISCLOSURE OF THE INVENTION

An object, therefore, of the present invention is to provide methods and pharmaceutical preparations that depend on a new mechanism of action for preventing or treating pruritic symptoms, in particular, atopic symptoms. A specific object of the present invention is to provide highly safe and efficacious methods and pharmaceutical preparations that can prevent or treat the onset of xerosis which is a dermal disease that is accompanied by cutaneous anaphylaxis of obscure etiology, itch sensation or scratching behavior that result from reduced lipid between horny cells of the skin and diminished water content of the stratum corneum.

With a view to attaining these objects, the present inventors made an investigation adopting the method of assessment to be described later and found that certain kinds of prostaglandins had an outstanding antipruritic effect and were particularly effective in controlling the itch sensation accompanying atopic symptoms. In addition, the present inventors studied various drugs that could effectively reduce the transpiration of water content from the skin and found that a prostaglandin D (DP) receptor selective agonist could effectively control excessive dryness of the skin, thus proving effective in preventing or treating conditions such as diminished water content of the stratum corneum. The present invention has been accomplished on the basis of these findings.

Thus, according to one embodiment of the invention, there are provided a method for preventing or treating xerosis which comprises applying a prostaglandin D receptor selective agonist to a mammal, as well as a pharmaceutical preparation for preventing or treating xerosis which contains a prostaglandin D receptor selective agonist as an active ingredient.

In the present invention, the "prostaglandin D receptor selective agonist" is a substance that has weak action on non-prostaglandin receptors such as a thromboxane (TP) receptor but which act as a strong agonist on a prostaglandin D receptor, in particular, among various prostaglandin receptors. Specifically, it is a compound that has less than 10 nM of $IC_{50}$ in the action of inhibiting ADP-induced human platelet aggregation as a prostaglandin D receptor agonistic action [the Born method (Nature, vol. 194, p. 927, 1962)] and at least 10 μM of $IC_{50}$ in the human TP antagonistic action [the method described in J. Pharmacol. Exp. Ther., vol. 245, pp. 786-792, 1988]. Examples of the prostaglandin D receptor selective agonist are prostaglandins, in particular, compounds of formula [1] set forth below.

According to another embodiment of the present invention, there are provided a method for preventing or treating pruritic symptoms (including atopic symptoms), in particular, xerosis which comprises applying to a mammal a prostaglandin derivative represented by formula [1]

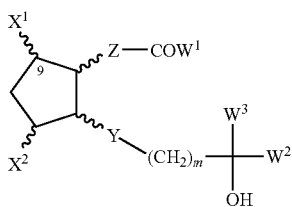

wherein $X^1$ and $X^2$ which are different from each other represent a hydrogen atom, a halogen atom or a hydroxyl group;

Y is an ethylene group, a vinylene group or an ethynylene group; Z is the formula $(CH_2)_k A(CH_2)_h B(CH_2)_q$, $(CH_2)_k A(CH_2)_r A'(CH_2)_t$, $(CH_2)_k B(CH_2)_h B'(CH_2)_q$ or $(CH_2)_{k-1} B'(CH_2)_{q-1} A'$ wherein k is an integer of 1 to 4, h is an integer of 0 to 4, q is an integer 1 to 4, r is an integer of 0 to 4, and t is an integer of 0 to 2;

A and A' which may be the same or different represent an ethylene group, a vinylene group or an ethynylene group;

B and B' which may be the same or different represent an oxygen atom or a group represented by the formula $S(O)_u$ wherein u is an integer of 0 to 2;

$W^1$ is a hydroxyl group, a $C_{1-10}$ alkyloxy group, a $C_{3-10}$ cycloalkyloxy group, an aryloxy group or an arylalkyloxy group;

$W^2$ is a $C_{1-10}$ alkyl group, a $C_{2-10}$ alkenyl group, a $C_{2-10}$ alkynyl group, a $C_{3-10}$ cycloalkyl group, a $C_{1-5}$ alkyl group substituted by $C_{3-10}$ cycloalkyl group(s), or a group represented by the formula

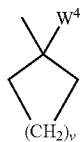

wherein $W^4$ is a $C_{1-10}$ alkyl group, a $C_{2-10}$ alkenyl group, a $C_{2-10}$ alkynyl group or a $C_{1-5}$ alkyl group substituted by $C_{3-10}$ cycloalkyl group(s); v is an integer of 0 to 4;

$W^3$ is a hydrogen atom or a methyl group, or $W^3$ when taken together with $W^2$ and the adjacent carbon atom forms a $C_{3-10}$ cycloalkyl group; m is 0 or 1, a pharmaceutically acceptable salt thereof or a hydrate thereof, as well as a pharmaceutical preparation to be used in the method for prevention or treatment.

According to yet another embodiment of the present invention, there are provided a method for preventing or treating pruritic symptoms (including atopic symptoms), in particular, xerosis which comprises applying to a mammal a prostaglandin derivative represented by formula [1], provided that 7-[(1R,2R,3R,5R)-5-chloro-2-[(1E,3S)-3-cyclohexyl-3-hydroxy-1-propenyl]-3-hydroxycyclopentyl]-(5Z)-5-heptenoic acid is excluded, a pharmaceutically acceptable salt thereof or a hydrate thereof, as well as a pharmaceutical preparation to be used in the method for prevention or treatment.

The present invention may have the following embodiments for the prostaglandin derivative represented by formula [1], pharmaceutically acceptable salts thereof or hydrates thereof.

(1) A prostaglandin derivative of formula [1] where Z is a group represented by the formula $(CH_2)_k A(CH_2)_h B(CH_2)_q$ (wherein k is an integer of 1 to 4, h is an integer of 0 to 4, q is an integer 1 to 4, A represents an ethylene group, a vinylene group or an ethynylene group, and B represents an oxygen atom or a group represented by the formula $S(O)_u$ wherein u is an integer of 0 to 2], a pharmaceutically acceptable salt thereof or a hydrate thereof.

(2) Compound (1) above which is a prostaglandin derivative of formula [1] where Z is a group represented by the formula $(CH_2)_k A(CH_2)_h B(CH_2)_q$ (wherein k, h and q are k+h+q=3), a pharmaceutically acceptable salt thereof or a hydrate thereof.

(3) A prostaglandin derivative of formula [1] where Z is a group represented by the formula $(CH_2)_k A(CH_2)_r A'(CH_2)_t$

[wherein k is an integer of 1 to 4, r is an integer of 0 to 4, t is an integer 1 to 4, A and A' which may be the same or different represent an ethylene group, a vinylene group or an ethynylene group], a pharmaceutically acceptable salt thereof or a hydrate thereof.

(4) Compound (3) above which is a prostaglandin derivative of formula [1] where Z is a group represented by the formula $(CH_2)_k A(CH_2)_r A'(CH_2)_t$ (wherein k, r and t are k+r+t=2), a pharmaceutically acceptable salt thereof or a hydrate thereof.

(5) A prostaglandin derivative of formula [1] where Z is a group represented by the formula $(CH_2)_k B(CH_2)_h B'(CH_2)_q$

[wherein k is an integer of 1 to 4, h is an integer of 0 to 4, q is an integer 1 to 4, B and B' which may be the same or different represent an oxygen atom or a group represented by the formula $S(O)_u$ wherein u is an integer of 0 to 21, a pharmaceutically acceptable salt thereof or a hydrate thereof.

(6) Compound (5) above which is a prostaglandin derivative of formula [1] where Z is a group represented by the formula $(CH_2)_k B(CH_2)_h B'(CH_2)_q$ (wherein k, h and q are k+h+q=4), a pharmaceutically acceptable salt thereof or a hydrate thereof.

(7) A prostaglandin derivative of formula [1] where Z is a group represented by the formula $(CH_2)_{k-1} B'(CH_2)_{q-1} A'$

[wherein k is an integer of 1 to 4, q is an integer of 1 to 4, A' represents an ethylene group, a vinylene group or an ethynylene group, and B' represents an oxygen atom or a group represented by the formula $S(O)_u$ wherein u is an integer of 0 to 2], a pharmaceutically acceptable salt thereof or a hydrate thereof.

(8) Compound (7) above which is a prostaglandin derivative of formula [1] where Z is a group represented by the formula $(CH_2)_{k-1} B'(CH_2)_{q-1} A'$ (wherein k and q are k+q=5), a pharmaceutically acceptable salt thereof or a hydrate thereof.

(9) Compound of formula [1] or a compound according to any one of (1) to (8) above, which is a prostaglandin derivative of formula [1] where $X^1$ is a halogen atom, $X^2$ is a hydroxyl group and Y is an ethynylene group, a pharmaceutically acceptable salt thereof or a hydrate thereof.

(10) Compound of formula [1] or a compound according to any one of (1) to (8) above, which is a prostaglandin derivative of formula [1] where $X^1$ is a halogen atom, $X^2$ is a hydroxyl group and Y is a vinylene group, a pharmaceutically acceptable salt thereof or a hydrate thereof.

(11) Compound of formula [1] or a compound according to any one of (1) to (10), which is a prostaglandin derivative of formula [1] wherein $W^2$ is a $C_{1-10}$ alkyl group, a $C_{2-10}$ alkenyl group, a $C_{2-10}$ alkynyl group, a $C_{3-10}$ cycloalkyl group, a $C_{1-5}$ alkyl group substituted by $C_{3-10}$ cycloalkyl group(s), or a group represented by the formula

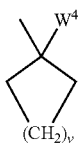

wherein $W^4$ is a $C_{1-10}$ alkyl group, a $C_{2-10}$ alkenyl group, a $C_{2-10}$ alkynyl group or a $C_{1-5}$ alkyl group substituted by $C_{3-10}$ cycloalkyl group(s); v is an integer of 0 to 4; $W^3$ is a hydrogen atom or a methyl group, a pharmaceutically acceptable salt thereof or a hydrate thereof.

(12) A compound represented by formula [A]

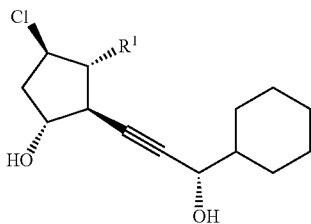

[wherein $R^1$ is any one group selected from the group represented by —$(CH_2)_4$—S—$CH_2$—$CO_2H$, the group represented by —$(CH_2)_4$—S—$CH_2$—$CO_2CH_3$, the group represented by —$(CH_2)_4$—C≡$CO_2H$, the group represented by —$CH_2$—S—$(CH_2)_2$—S—$CH_2$—$CO_2H$, and the group represented by —$CH_2$—S—$(CH_2)_4$—$CO_2H$].

(13) A compound represented by formula

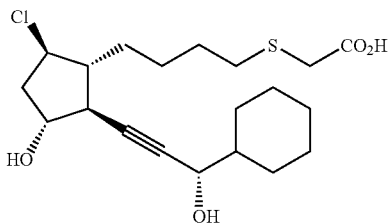

(which is hereunder referred to as compound No. 7).

BEST MODE FOR CARRYING OUT THE INVENTION

Figure 1:
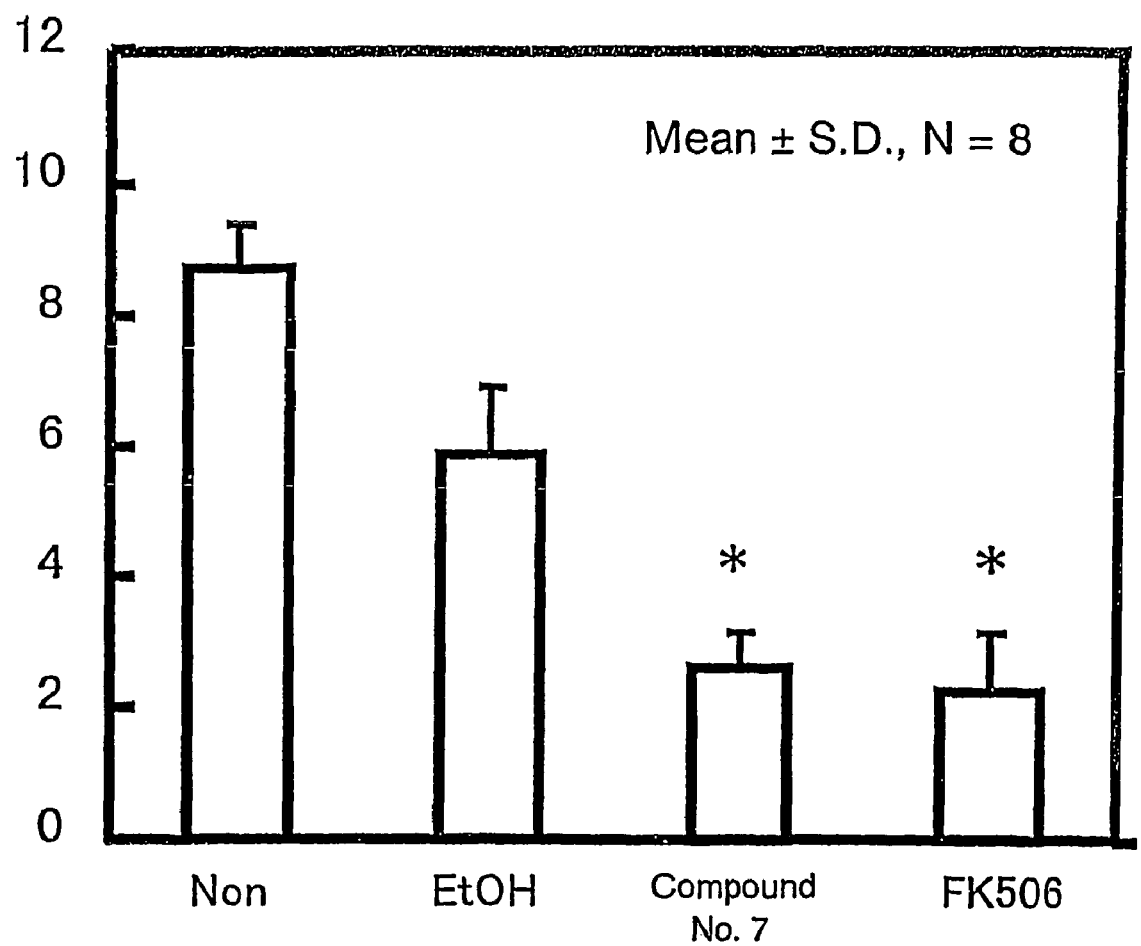
FIG. 1 shows the results with dermatitic symptoms (dermatitis scores) as observed at 4 weeks after drug administration, in which Non refers to no treatment, EtOH ethanol, FK506 tacrolimus, and * means a significant difference at p<0.05 from the vehicle administered group.

The inventors assessed the antipruritic effect of various pharmaceutical preparations on itch-evoked but spontaneous scratching behavior by measuring the itch-evoked scratching behavior of NC/Nga mice that would spontaneously develop an atopic dermatitis-like skin disease.

The numbers of scratchings done by the individual animals during 24-hr periods before and after the dermal application of pharmaceutical preparations were compared to confirm the outstanding efficacy of prostaglandins represented by formula [1].

The present inventors studied the mechanism of action in itching and excessive dryness of the skin; as a result, they found that NC/Nga mice which would develop dermatitis spontaneously did not experience substantial changes with aging in the contents of prostaglandins $PGE_2$, $PGF_{2\alpha}$, and PGI$_2$ in the skin tissue but experienced a significant drop in the PGD$_2$ content with aging. These results suggest the possibility that in the NC/Nga mice which will develop dermatitis spontaneously, the decreased in vivo PGD$_2$ content associated with aging may trigger itching and excessive dryness of the skin. In other words, the endogenous PGD$_2$ content has the physiological action of maintaining the skin's barrier function and the supply of exogenous stable PGD$_2$ derivatives would contribute to preventing or treating the onset of xerosis.

The present invention is described below in detail.

One embodiment of the present invention is characterized by a method for preventing or treating xerosis which comprises applying the prostaglandin D receptor selective agonist to a mammal, as well as a pharmaceutical preparation for preventing or treating xerosis which comprises the prostaglandin D receptor selective agonist as an active ingredient. Examples of the prostaglandin D receptor selective agonist are prostaglandins, in particular, compounds of formula [1] set forth below.

Another embodiment of the present invention is characterized by a method for preventing or treating pruritic symptoms (including atopic symptoms), in particular, xerosis which comprises applying to a mammal the prostaglandin derivative represented by formula [1], a pharmaceutically acceptable salt thereof or a hydrate thereof, as well as a pharmaceutical preparation to be used in the method for prevention or treatment.

The prostaglandin derivatives represented by formula [1], pharmaceutically acceptable salts thereof or hydrates thereof which are to be used in the present invention are described below.

In the formula [1], the halogen atom means a fluorine atom, a chlorine atom, a bromine atom or an iodine atom.

The vinylene group means a cis- or trans-vinylene group.

The $C_{1-10}$ alkyloxy group represents linear or branched alkyloxy groups having 1 to 10 carbon atoms, which include, for example, a methoxy group, an ethoxy group, a propoxy group, an isopropoxy group, a butoxy group, a sec-butoxy group, a tert-butoxy group, a pentyloxy group, a tert-pentyloxy group, a 5-methylhexyloxy group, an octyloxy group, a decyloxy group, etc.

Examples of the $C_{3-10}$ cycloalkyloxy group include a cyclopropyloxy group, a cyclobutyloxy group, a cyclopentyloxy group, a cyclohexyloxy group, a cycloheptyloxy group, a cyclononyloxy group, etc.

Examples of the aryloxy group include a phenoxy group, a bromophenoxy group, a chlorophenoxy group, a tolyloxy group, a cumenyloxy group, a methoxyphenoxy group, etc.

Examples of the arylalkyloxy group include a benzyloxy group, a bromobenzyloxy group, a chlorobenzyloxy group, a nitrobenzyloxy group, a dinitrobenzyloxy group, a methoxybenzyloxy group, a phenethyloxy group, a phenylpropyloxy group, a phenylpentyloxy group, etc.

The $C_{1-10}$ alkyl group represents linear or branched alkyl groups having 1 to 10 carbon atoms, which include, for example, a methyl group, an ethyl group, a propyl group, an isopropyl group, a butyl group, a sec-butyl group, a tert-butyl group, a pentyl group, a tert-pentyl group, an isohexyl group, a heptyl group, an octyl group, a decyl group, etc.

The $C_{2-10}$ alkenyl group means those linear or branched alkyl groups with 2 to 10 carbon atoms which have one or more double bonds in desired positions and they may be exemplified by a vinyl group, an allyl group, a 1-propenyl group, an isopropenyl group, a 3-butenyl group, a 1,3-butadienyl group, a 7-octenyl group, etc.

The $C_{2-10}$ alkynyl group means those linear or branched alkyl groups with 2 to 10 carbon atoms which have one or more triple bonds in desired positions and may be exemplified by an ethynyl group, a 2-propynyl group, a 2-pentynyl group, a 4-octynyl group, etc.

Examples of the $C_{3-10}$ cycloalkyl group include unsubstituted cycloalkyl groups such as a cyclopropyl group, a cyclobutyl group, a cyclopentyl group, a cyclohexyl group, a cycloheptyl group and a cyclononyl group, as well as those cycloalkyl groups having one or more substituents selected from among halogen atoms, $C_{1-10}$ alkyl groups, $C_{1-10}$ alkyloxy groups, etc. which are exemplified by a 4-fluorocyclohexyl group, a 4,4-difluorocyclohexyl group, a 4-methoxycyclohexyl group, a 2-methylcyclohexyl group, a 4-trifluoromethylcyclohexyl group, etc.

Examples of the $C_{1-5}$ alkyl group substituted by $C_{3-10}$ cycloalkyl group(s) include a cyclopropylmethyl group, a cyclobutylethyl group, a cyclopentylmethyl group, a cyclohexylmethyl group, a cycloheptylmethyl group, a cyclononylbutyl group, a 4-fluorocyclohexylmethyl group, etc.

The pharmaceutically acceptable salt may be exemplified by salts with alkali metals such as sodium and potassium, salts with alkaline earth metals such as calcium and magnesium, and salts with ammonia, methylamine, dimethylamine, cyclopentylamine, benzylamine, piperidine, monoethanolamine, diethanolamine, monomethylmonoethanolamine, tromethamine, lysine, tris(hydroxymethyl)aminomethane, etc.

If Z is the formula $(CH_2)_k A(CH_2)_h B(CH_2)_q$, preferably, k+h+q=3, and more preferably, k=1, h=1 and q=1. If Z is the formula $(CH_2)_k A(CH_2)_r A'(CH_2)_t$, preferably, k+r+t=2, and more preferably, k=1, r=1 and t=0. If Z is the formula $(CH_2)_k B(CH_2)_h B'(CH_2)_q$, preferably, k+h+q=4, and more preferably, k=1, h=2 and q=1. If Z is the formula $(CH_2)_{k-1} B' (CH_2)_{q-1} A'$, preferably, k+q=5, and more preferably, k=2 and q=3.

Some of the prostaglandin derivatives which serve as the active ingredient in the present invention are known compounds disclosed in the following publications:

WO94/02457, WO94/08959, WO95/18101, WO99/61029, WO99/61419, WO01/19790, U.S. Pat. No. 5,807,892, JP 2-502009 A, JP 6-192218 A, JP 7-242622 A, JP 7-242623 A, JP 7-233144 A, JP 7-285929 A, JP 8-208599 A, JP 9-286775 A, JP 58-8059 A, JP 60-501813 A, JP 61-500787 A, JP 2000-95755 A, JP 2000-128858 A, JP 2000-273083 A, JP 2001-122786 A, JP 2001-89443 A, JP 2001-135944 A, and JP 2001-151749 A.

The compounds of formula [A] which are preferred in the present invention are described in WO95/18101, WO99/61419 and WO01/19790 and can be produced by the methods disclosed in those publications.

Note that prostaglandin derivatives represented by the following formula

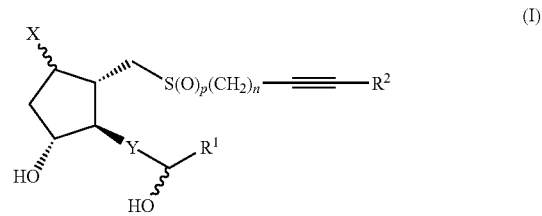

(I)

wherein X is an α- or β-substituted halogen atom, Y is an ethylene group, a vinylene group or an ethynylene group, $R^1$ is a $C_{3-10}$ cycloalkyl group, a $C_{3-10}$ cycloalkyl group substituted by $C_{1-4}$ linear or branched alkyl group(s), or a $C_{4-13}$ cycloalkylalkyl group, $R^2$ is a group represented by $CO_2R^3$, wherein $R^3$ is a hydrogen atom, a $C_{1-4}$ linear or branched alkyl group or a $C_{2-4}$ linear or branched alkenyl group, n is an integer of 1 to 4, and p is 0, 1 or 2 can be produced by processes according to reaction schemes 1 and 2.

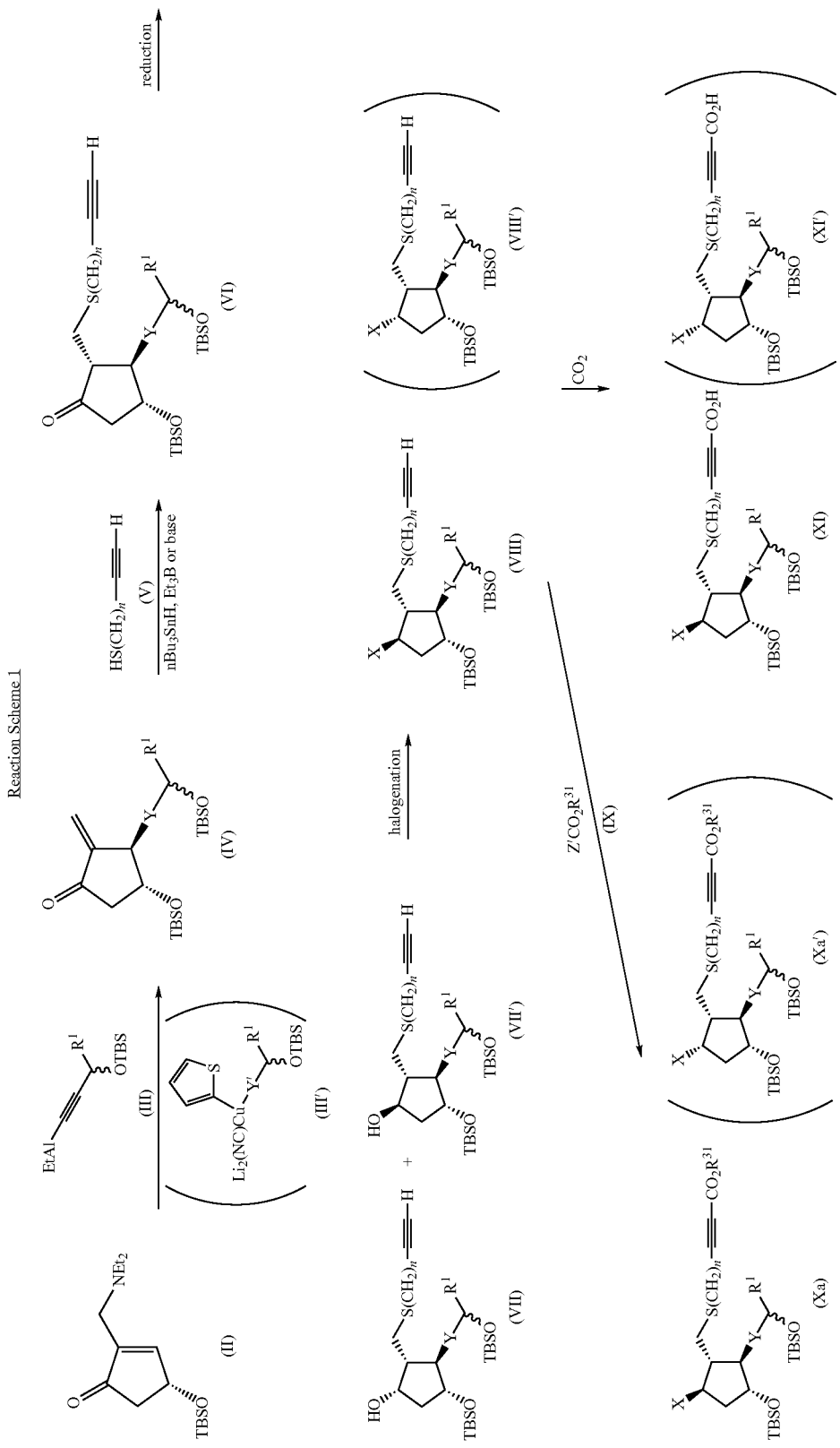

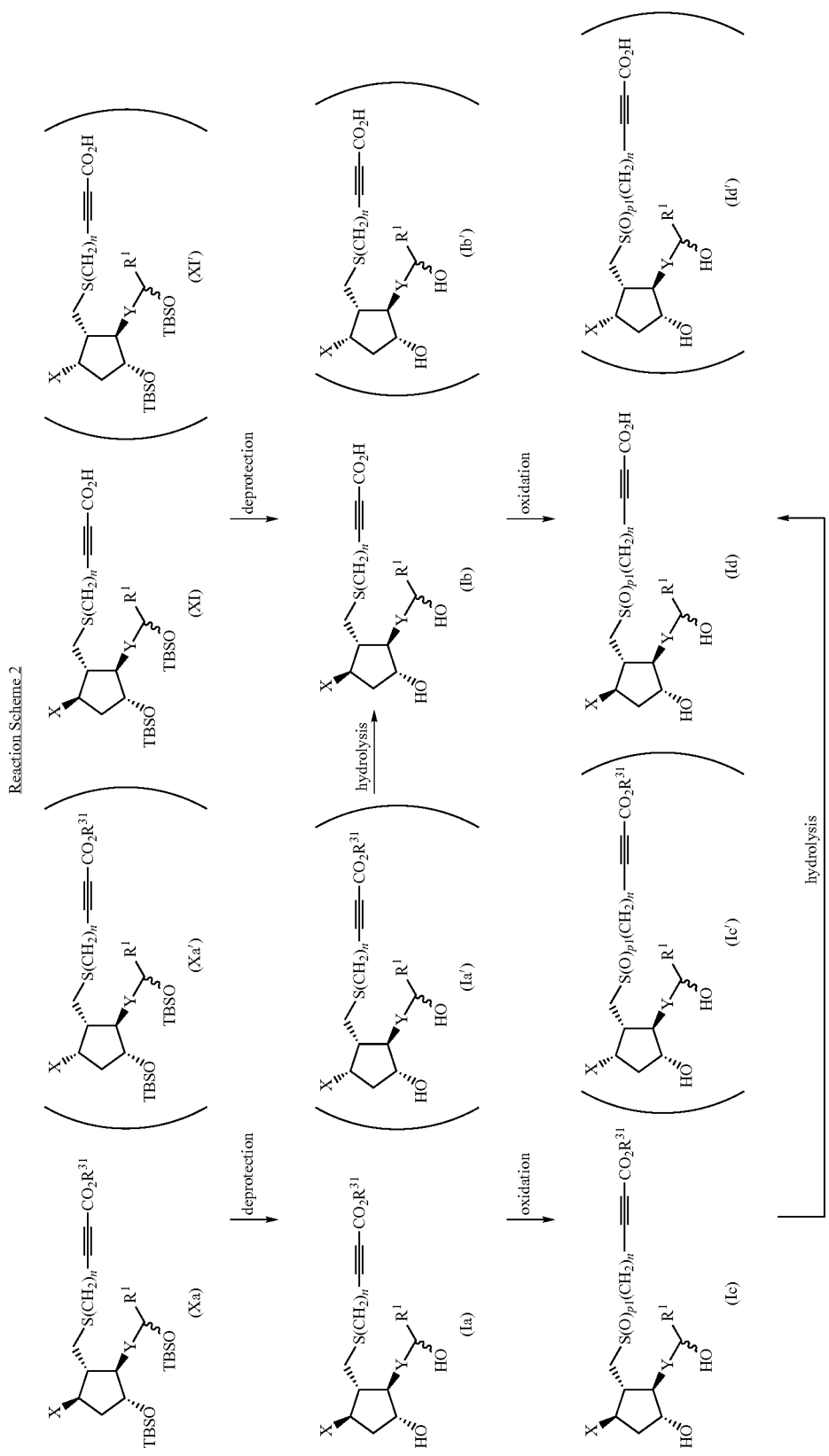

(in the above reaction schemes, TBS represents a tert-butyldimethylsilyl group, Y' represents an ethylene group or a vinylene group, $R^{31}$ represents a $C_{1-4}$ alkyl group or a $C_{2-4}$ alkenyl group, p1 represents 1 or 2, Z' represents a halogen atom, and X, Y, $R^1$ and n have the same meanings as defined above.)

The two reaction schemes are explained below:

(1) First, according to the method of Satoh et al. [Journal of Organic Chemistry (J. Org. Chem.), vol. 53, p. 5590 (1988)], a known compound of formula (II) is reacted with 0.8 to 2.0 equivalent amounts of a compound represented by formula (III) or (III') in an inert solvent (e.g. benzene, toluene, tetrahydrofuran, diethyl ether, methylene chloride or n-hexane) at –78 to 30° C., to give a stereospecific compound of formula (IV). In order to obtain a compound where Y is an ethylene group or a vinylene group (i.e. Y is Y'), a compound of formula (III') is employed and reaction is performed at –78 to 30° C.; in order to obtain a compound where Y is an ethynylene group, a compound of formula (III) is employed and reaction is performed at 0 to 30° C.

(2) The compound of formula (IV) is reacted with 1 to 6 equivalent amounts of a compound represented by formula (V) in an organic solvent (e.g. benzene, toluene, xylene, n-hexane, n-pentane or acetone) at –78 to 100° C., optionally employing 0.05 to 2 equivalent amounts of a radical generator (e.g. azobisisobutyronitrile, azobiscyclohexanecarbonitrile, benzoyl peroxide or triethylborane), further optionally employing 1 to 5 equivalent amounts of a radical reducing agent (e.g. tributyltin hydride, triphenyltin hydride, dibutyltin hydride or diphenyltin hydride), thereby giving a compound of formula (VI). In a certain case, a compound of formula (VI) can also be obtained by performing the reaction in an organic solvent (e.g. benzene, toluene, xylene, n-hexane, n-pentane or acetone) at –78 to 100° C. employing 0.05 to 2 equivalent amounts of a base (e.g. an organic amine such as triethylamine, diisopropylamine, pyridine or dimethylaniline, or a base resin such as polyvinylpyrrolidone, diisopropylaminomethyl-polystyrene or (piperidinomethyl)polystyrene).

(3) The compound of formula (VI) is reacted with 0.5 to 5 equivalent amounts of a reducing agent such as potassium borohydride, sodium borohydride, sodium cyanoborohydride, lithium tri-sec-butyl borohydride or diisobutylaluminum hydride-BHT (2,6-di-tert-butyl-p-cresol) in an organic solvent (e.g. tetrahydrofuran, diethyl ether, ethyl alcohol, methyl alcohol or toluene) at –78 to 40° C. to give compounds of formulas (VII) and (VII'). These compounds of formulas (VII) and (VII') can be purified by a commonly employed separation technique such as column chromatography.

(4) The compound of formula (VII) (or formula (VII')) is mesylated or tosylated with, for example, 1 to 6 equivalent amounts of methanesulfonyl chloride or p-toluenesulfonyl chloride in a suitable solvent such as pyridine at –20 to 40° C., optionally in the presence of 0.8 to 6 equivalent amounts of 4-dimethylaminopyridine, followed by chlorination with 1 to 16 equivalent amounts of tetra-n-butylammonium chloride to give a compound of formula (VIII) (or formula (VIII')) (X is a chlorine atom). Bromination and fluorination can also be performed by ordinary methods. For example, bromination can be obtained by reacting 1 to 10 equivalent amounts of carbon tetrabromide in acetonitrile in the presence of 1 to 10 equivalent amounts each of triphenylphosphine and pyridine. Fluorination may, for example, be obtained by reacting 5 to 20 equivalent amounts of diethylaminosulfur trifluoride (DAST) in methylene chloride.

(5) The compound of formula (VIII) (or formula (VIII')) is reacted with a base (e.g. an alkyl lithium such as n-butyllithium) at a temperature between –78° C. and room temperature in a suitable inert organic solvent (e.g. tetrahydrofuran or diethyl ether) and thereafter reacted with a compound of formula (IX) at –78 to 40° C. to give a compound of formula (Xa) (or formula (Xa')); if the formula (IX) is replaced by carbon dioxide as the reactant, a compound of formula (XI) (or formula (XI')) can be obtained.

(6) The compound of formula (Xa) (or formula (Xa')) is freed of the hydroxyl protecting tert-butyldimethylsilyl group in methanol, ethanol, acetonitrile or a mixed solvent thereof or a mixture thereof with water under ordinary conditions employing hydrofluoric acid, pyridinium poly(hydrogenfluoride), hydrochloric acid, etc. so as to give a PG derivative of formula (Ia) (or formula (Ia')) according to the present invention.

(7) By hydrolyzing the compound of formula (Ia) (or formula (Ia')) through reaction with an enzyme in a buffer solution such as a phosphate buffer or a Tris-HCl buffer, optionally employing an organic solvent (a water-miscible one such as acetone, methanol or ethanol), a PG derivative of formula (Ib) (or formula (Ib')) claimed in the invention can be obtained. Exemplary enzymes are those produced by microorganisms (e.g. enzymes produced by microorganisms of *Candida* sp. and *Pseudomonas* sp.) and those prepared from animal organs (e.g. enzymes prepared from swine liver and pancreas). To mention specific examples of commercial enzymes, they include lipase VII (product of Sigma, derived from a microorganism of *Candida* sp.), lipase AY (product of Amano Pharmaceutical Co., Ltd., derived from a microorganism of *Candida* sp.), lipase PS (product of Amano Pharmaceutical Co., Ltd., derived from a microorganism of *Pseudomonas* sp.), lipase MF (product of Amano Pharmaceutical Co., Ltd., derived from a microorganism of *Pseudomonas* sp.), PLE (product of Sigma, prepared from swine liver), lipase II (product of Sigma, prepared from swine pancreas), and lipoprotein lipase (product of Tokyo Kasei Kogyo Co., Ltd., prepared from swine pancreas).

The amount of the enzyme to be used may be chosen as appropriate for its potency and the amount of its substrate [formula (Ia) (or formula (Ia'))] and the usual amount is 0.1 to 20 times the weight of the substrate. The reaction temperature is 25 to 50° C., preferably 30 to 40° C.

A PG derivative of formula (Ib) (or formula (Ib')) claimed in the invention may be obtained by hydrolyzing the compound of formula (Ia) (or formula (Ia')) with a base in a solvent commonly employed in hydrolysis. Exemplary bases that can be employed are lithium hydroxide and potassium carbonate, and exemplary solvents include acetonitrile, acetone, methanol, ethanol, water and mixtures thereof.

A PG derivative of formula (Ib) (or formula (Ib')) claimed in the invention can also be obtained by deprotecting the compound of formula (XI) (or formula (XI')) as in (6) above.

(8) The compound of formula (Ia) (or formula (Ia')) is reacted with an oxidizing agent such as sodium metaperiodate, hydrogen peroxide, peracetic acid, m-chloroperbenzoic acid and tert-butyl hydroperoxide in diethyl ether, methanol, ethanol, methylene chloride, water or mixtures thereof at –20 to 50° C. to give a PG derivative of formula (Ic) (or formula (Ic')) claimed in the invention.

(9) By hydrolyzing the compound of formula (Ic) (or formula (Ic')) as in (7) above, a PG derivative of formula (Id) (or formula (Id')) claimed in the invention is obtained. A PG derivative of formula (Id) (or formula (Id')) claimed in the invention can also be obtained by oxidizing the formula (Ib) (or formula (Ib')) as in (8) above.

The following compounds can be listed as representative compounds of the formula [1] claimed in the invention.

TABLE 1

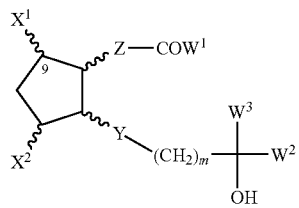

[1]

| Compound No. | X1 | X2 | Y | A | B | m | k | h | q | u | W1 | W2 | W3 | 8-position | 9-position | 11-position | 12-position | OH |
|---|---|---|---|---|---|---|---|---|---|---|---|---|---|---|---|---|---|---|
| 1 | Cl | HO | CH2CH2 | Z-CH=CH | S | 0 | 1 | 1 | 1 | 0 | OMe | cyc6 | H | α | β | α | β | α |
| 2 | Cl | HO | CH2CH2 | Z-CH=CH | S | 0 | 1 | 1 | 1 | 0 | OH | cyc6 | H | α | β | α | β | α |
| 3 | Cl | HO | E-CH=CH | Z-CH=CH | O | 0 | 1 | 1 | 1 |   | OH | cyc6 | H | α | β | β | β | α |
| 4 | Cl | HO | C≡C | Z-CH=CH | O | 0 | 1 | 1 | 1 |   | OtBu | cyc6 | H | α | β | α | β | α |
| 5 | Cl | HO | C≡C | CH2CH2 | O | 0 | 1 | 1 | 1 |   | OtBu | cyc6 | H | α | β | α | β | α |
| 6 | Cl | HO | C≡C | CH2CH2 | S | 0 | 1 | 1 | 1 | 0 | OMe | cyc6 | H | α | β | α | β | α |
| 7 | Cl | HO | C≡C | CH2CH2 | S | 0 | 1 | 1 | 1 | 0 | OH | cyc6 | H | α | β | α | β | α |
| 8 | Cl | HO | C≡C | Z-CH=CH | O | 0 | 1 | 1 | 1 |   | OH | cyc6 | H | α | β | α | β | α |
| 9 | H | HO | C≡C | CH2CH2 | S | 0 | 1 | 1 | 1 | 0 | OH | cyc6 | H | α |   | α | β | α |
| 10 | Cl | HO | C≡C | C≡C | O | 0 | 1 | 1 | 1 |   | OH | cyc6 | H | α | β | α | β | α |
| 11 | Cl | HO | CH2CH2 | Z-CH=CH | O | 0 | 1 | 1 | 1 |   | OH | cyc6 | H | α | β | α | β | α |
| 12 | Cl | HO | E-CH=CH | CH2CH2 | S | 0 | 1 | 1 | 1 | 0 | OH | cyc6 | H | α | β | α | β | α |

E-CH=CH: trans-vinylene group
Z-CH=CH: cis-vinylene group
cyc6: cyclohexyl group

TABLE 2

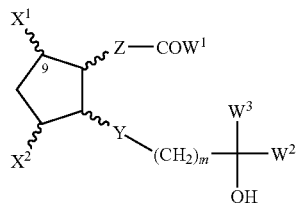

[1]

| Compound No. | X1 | X2 | Y | A | A' | m | k | r | t | W1 | W2 | W3 | 8-position | 9-position | 11-position | 12-position | OH |
|---|---|---|---|---|---|---|---|---|---|---|---|---|---|---|---|---|---|
| 13 | Cl | HO | E-CH=CH | CH2CH2 | C≡C | 0 | 1 | 1 | 0 | OMe | cyc5m | H | α | α | α | β | α |
| 14 | Cl | HO | C≡C | CH2CH2 | C≡C | 0 | 1 | 2 | 0 | OH | cyc6 | H | α | β | α | β | α |
| 15 | Cl | HO | C≡C | CH2CH2 | C≡C | 0 | 1 | 1 | 0 | OH | cyc6 | H | α | β | α | β | α |
| 16 | Cl | HO | C≡C | CH2CH2 | E-CH=CH | 0 | 1 | 1 | 0 | OMe | cyc6 | H | α | β | α | β | α |
| 17 | Cl | HO | C≡C | CH2CH2 | E-CH=CH | 0 | 1 | 1 | 0 | OiPr | cyc6 | H | α | β | α | β | α |
| 18 | Cl | HO | C≡C | CH2CH2 | E-CH=CH | 0 | 1 | 1 | 0 | OtBu | cyc6 | H | α | β | α | β | α |
| 19 | Cl | HO | C≡C | CH2CH2 | C≡C | 0 | 1 | 1 | 0 | OtBu | cyc6 | H | α | β | α | β | α |
| 20 | Cl | HO | C≡C | CH2CH2 | C≡C | 0 | 1 | 1 | 1 | OMe | Me-cyc6 | H | α | β | α | β | α |

Z-CH=CH: cis-vinylene group
E-CH=CH: trans-vinylene group
cyc6: cyclohexyl group
Me-cyc6: 2-methylcyclohexyl group
cyc5m: cyclopentylmethyl group

TABLE 3

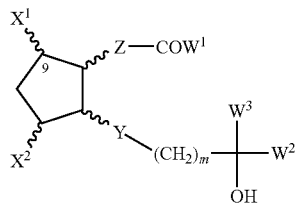

| Compound No. | X1 | X2 | Y | B | B' | m | k | h | q | u | W1 | W2 | W3 | 8-position | 9-position | 11-position | 12-position | OH |
|---|---|---|---|---|---|---|---|---|---|---|---|---|---|---|---|---|---|---|
| 21 | Cl | HO | C≡C | S | O | 0 | 1 | 2 | 1 | 0 | OMe | cyc6 | H | α | β | α | β | α |
| 22 | Cl | HO | C≡C | S | O | 0 | 1 | 2 | 1 | 0 | OH | cyc6 | H | α | β | α | β | α |
| 23 | Cl | HO | C≡C | S | S | 0 | 1 | 2 | 1 | 0 | OMe | cyc6 | H | α | β | α | β | α |
| 24 | Cl | HO | C≡C | S | S | 0 | 1 | 2 | 1 | 0 | OMe | cyc6 | H | α | α | α | β | α |
| 25 | Cl | HO | C≡C | S | S | 0 | 1 | 2 | 1 | 0 | OH | cyc6 | H | α | β | α | β | α |
| 26 | Cl | HO | C≡C | S | O | 0 | 1 | 2 | 1 | 0 | OMe | diF-cyc6 | H | α | β | α | β | α |
| 27 | Cl | HO | C≡C | S | O | 0 | 1 | 2 | 1 | 0 | OH | diF-cyc6 | H | α | β | α | β | α |
| 28 | Cl | HO | C≡C | S | O | 0 | 1 | 2 | 1 | 0 | OMe | CF3-cyc6 | H | α | β | α | β | α |
| 29 | Cl | HO | C≡C | S | O | 0 | 1 | 2 | 1 | 0 | OH | CF3-cyc6 | H | α | β | α | β | α |
| 30 | Cl | HO | C≡C | S | S | 0 | 1 | 3 | 1 | 0 | OMe | cyc6 | H | α | β | α | β | α | cyc6: cyclohexyl group
diF-cyc6: difluorocyclohexyl group
CF3-cyc6: 4-trifluoromethylcyclohexyl group

TABLE 4

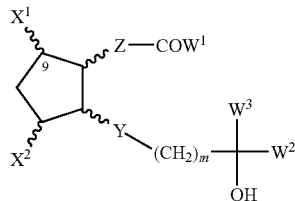

| Compound No. | X1 | X2 | Y | A' | B' | m | k | q | u | W1 | W2 | W3 | 8-position | 9-position | 11-position | 12-position | OH |
|---|---|---|---|---|---|---|---|---|---|---|---|---|---|---|---|---|---|
| 31 | Cl | HO | C≡C | CH2CH2 | S | 0 | 2 | 3 | 0 | OMe | cyc6 | H | α | β | α | β | α |
| 32 | Cl | HO | C≡C | CH2CH2 | S | 0 | 2 | 3 | 0 | OH | cyc6 | H | α | β | α | β | α |
| 33 | Cl | HO | E-CH=CH | CH2CH2 | S | 0 | 1 | 4 | 0 | OMe | cyc6 | H | α | β | α | β | α |
| 34 | Cl | HO | E-CH=CH | CH2CH2 | S | 0 | 4 | 1 | 0 | OMe | cyc6 | H | α | β | α | β | α |
| 35 | Cl | HO | E-CH=CH | CH2CH2 | S | 0 | 3 | 2 | 0 | OMe | cyc6 | H | α | β | α | β | α |
| 36 | Cl | HO | E-CH=CH | CH2CH2 | S | 0 | 2 | 3 | 0 | OH | cyc6 | H | α | β | α | β | α |
| 37 | Cl | HO | CH2CH2 | CH2CH2 | S | 0 | 2 | 3 | 0 | OMe | cyc6 | H | α | β | α | β | α |
| 38 | Cl | HO | CH2CH2 | CH2CH2 | S | 0 | 2 | 3 | 0 | OH | cyc6 | H | α | β | α | β | α |
| 39 | Cl | HO | C≡C | C≡C | S | 0 | 2 | 3 | 0 | OH | cyc6 | H | α | β | α | β | α |
| 40 | Cl | HO | C≡C | CH2CH2 | S | 0 | 2 | 1 | 0 | OH | cyc6 | H | α | β | α | β | α |

E-CH=CH: trans-vinylene group
cyc6: cyclohexyl group

As long as they can relieve or eliminate an itch sensation, the antipruritics of the invention are not limited in any way but they are particularly effective against the atopy-evoked itching. From this viewpoint, the antipruritics of the invention encompass pharmaceutical preparations for preventing or treating atopic symptoms.

In the invention, the term "pruritic symptoms" means those symptoms which involve circumscribed or generalized itching and associated inflammations on the skin and mucous membranes. Examples include scabies, urticaria, eczema, xerosis (senile xeroderma and asteatotic eczema), psoriasis, dermal pruritus, and prurigo.

In the invention, the term "atopic symptoms" means those symptoms which involve atopy-evoked, circumscribed or generalized itching and associated inflammations on the skin and mucous membranes; in other words, the term refers to atopy-evoked pruritic symptoms (including nervous pruritus). Examples include atopic dermatitis and atopic conjunctivitis.

In the invention, the term "atopic dermatitis" refers to a disorder that involves itching eczema as a principal lesion which undergoes repeated exacerbation and remission; this is highly likely to develop in individuals predisposed to atopy.

In the invention, the term "xerosis" refers to a condition involving excessive dryness of the skin and typical examples include senile xeroderma and asteatotic eczema, as well as dry skin.

In the invention, the term "senile xeroderma" refers to a case of xerosis that occurs with aging from diminished lipid between horny cells and lowered water content of the stratum corneum.

The prostaglandin D receptor selective agonist as the active ingredient in the invention is effective against xerosis, particularly against senile xeroderma.

The antipruritics and pharmaceutical preparations against xerosis according to the invention can be administered either orally, parenterally or topically.

The dose to be administered of the active ingredient in the antipruritics and pharmaceutical preparations against xerosis according to the invention can be adjusted as appropriate for the body weight of the patient, his or her age, sex, etc. Usually, the dosage is 1 ng to 10 mg, preferably 0.1 to 100 μg, per administration and one to several administrations are tolerated per day. Depending on such factors as age, sex and body weight, the pharmaceutical preparations against xerosis can typically be administered by applying appropriate doses of the preparations to the diseased area at concentrations of the active ingredient ranging from about 0.1 to about 0.0001%.

The antipruritics and pharmaceutical preparations against xerosis according to the invention can be prepared as pharmaceutical compositions employing the active ingredient in combination with carriers (bases), vehicles and other additives that are employed in ordinary pharmaceutical formulation procedures.

Exemplary carriers (bases) and vehicles for pharmaceutical formulation procedures include water, ethanol, lactose, microcrystalline cellulose, liquid paraffin, hydrogenated oils, beeswax, squalane, stearyl alcohol, ethylene glycol and others that are in common use.

Exemplary additives are commonly employed ingredients including disintegrants (e.g. starch), binders (hydroxypropyl cellulose and low-substituted hydroxypropyl cellulose), lubricants (e.g. talc and glycerol stearate), antioxidants, gelling agents, solubilizers, solvent promoters, pH adjusting agents, preservatives (e.g. parabens), coating agents (e.g. gelatin and hydroxypropyl cellulose), coloring agents, flavoring/odorizing agents, skin color lightening agents (e.g. sodium ellagate), surfactants (e.g. sorbitan fatty acid esters), plasticizers, humectants (e.g. glycerin, propylene glycol, polyethylene glycol and hyaluronic acid), etc.

The antipruritics and pharmaceutical preparations against xerosis according to the invention can be administered in various dosage forms such as those for internal application, injections and those for external application (nasal drops and eye drops), as specifically exemplified by tablets, granules, powders, capsules, liquids, gels, plasters, ointments, creams, cataplasms and aerosols.

The pharmaceutical preparations against xerosis according to the invention can typically incorporate not only the active ingredient but also the necessary base, gelling agent, solubilizer, solvent promoter, pH adjusting agent and any other pharmaceutically active ingredients.

Dosage forms for external application are preferred for the antipruritics and pharmaceutical preparations against xerosis according to the invention because of the various advantages they have, such as direct applicability to the diseased area, ease of application and reduced possibility for vitiation by metabolism and the occurrence of systemic side effects.

Dosage forms "for external application" include liquids for external application, aerosols, powders for external application, ointments, creams, gels, plasters, cataplasms, etc.

The following examples and test examples are provided for the purpose of further illustrating the present invention but are in no way to be taken as limiting. Various alterations and modifications can be made by the skilled artisan on the basis of the foregoing description of the invention and are also encompassed by the invention.

Unless otherwise noted, the drug concentration (%) means w/v % (weight/volume %).

Example 1

A hundredth of a gram of compound No. 7 was weighed, dissolved in 20 g of glycerin and mixed with 80 g of white petrolatum uniformly to prepare 100 g of an ointment.

| | |
|---|---|
| Compound No. 7 | 0.01 g |
| White petrolatum | 80 g |
| Glycerin | 20 g |

Example 2

The ingredients listed below were weighed and mixed uniformly; then, purified water and ethanol were added in the volumes indicated below to make 1000 ml of a liquid.

| | |
|---|---|
| Compound No. 7 | 0.1 g |
| Ethanol | 200 ml |
| Purified water | 800 ml |

Example 3

The ingredients listed below were weighed and emulsified uniformly; then, a flavoring agent was added to make 500 g of a cream.

| | |
|---|---|
| Compound No. 3 | 0.5 g |
| Carbinoxamine maleate | 5 g |
| Sodium ellagate | 5 g |
| Sodium hyaluronate | 3 g |
| Methyl paraben | 2 g |
| Purified water | 218.5 g |
| Liquid paraffin(#70) | 50 g |
| Squalane | 100 g |
| Cetostearyl alcohol | 60 g |
| Beeswax | 20 g |
| Glycerol monostearate | 15 g |
| Sorbitan monolaurate | 20 g |
| Propyl paraben | 1 g |

Example 4

The ingredients listed below were weighed and emulsified uniformly; then, a flavoring agent was added to make 500 g of a cream.

| | |
|---|---|
| Compound No. 7 | 0.05 g |
| Carbinoxamine maleate | 5 g |
| Sodium ellagate | 5 g |
| Sodium hyaluronate | 3 g |
| Methyl paraben | 2 g |
| Purified water | 218.5 g |
| Liquid paraffin(#70) | 50 g |
| Squalane | 100 g |

-continued

| | |
|---|---|
| Cetostearyl alcohol | 60 g |
| Beeswax | 20 g |
| Glycerol monostearate | 15 g |
| Sorbitan monolaurate | 20 g |
| Propyl paraben | 1 g |

Example 5

An aerosol was prepared according to a recipe consisting of the following ingredients.

| | |
|---|---|
| Compound No. 7 | 0.01 (W/V %) |
| Diisopropyl adipate | 3 |
| Polyethylene glycol monolaurate | 8 |
| Ethanol | 10 |
| Isopropanol | 10 |
| Macrogol 400 | 5 |
| Dibutylhydroxytoluene | 0.1 |
| Diisopropanolamine | 0.2 |
| Purified water | 25 |
| Liquefied petroleum gas | q.s. to make 100 (W/V %) |

Test Example 1

Effect on the Spontaneous, Itch-Evoked Scratching Behavior of NC Mice (Method)

About 20-week old NC/Nga mice each weighing about 30 g and manifesting atopic dermatitis were purchased from SLC and subjected to the following experiment. A magnet was buried in both hind paws of each mouse and by detecting its magnetism, the movement of the paws was measured with an itch measuring system (product of Neuroscience; when the mouse makes an action, the magnets move accordingly and a current flows through the coil; the moving magnets cause a change in the current, which is detected, measured and analyzed). Among the scratching actions, those lasting 1.5 seconds or longer were considered itch-evoked and their number was counted continuously. Since the itch-evoked scratching behavior had a diurnal rhythm, the diurnal rhythm of each individual animal was measured for 24 hours of the day before test and only after that, each of the test drugs dissolved in 100% ethanol was applied to the dorsal skin in a dose of 0.2 ml/mouse. The subsequent 24-hr itch-evoked scratching behavior was measured and the number of itch-evoked scratchings after drug administration was compared with the initial count. The experimental data was processed to calculate the percent itch suppression on the basis of the total 24-hr itch-evoked scratching counts before and after drug application. For significance testing, the itch-evoked scratching counts that were obtained before and after drug application from individual animals in each group treated with a specific concentration of drug were processed by a paired t-test.

Percent itch suppression (%)=(itch-evoked scratching count before drug application−itch-evoked scratching count after drug application)×100/itch-evoked scratching count before drug application (Results)

The structures of the compounds used in the test are shown below and the test results are shown in Table 5.

TABLE 5

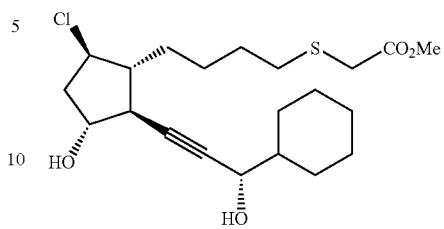

Compound No. 6

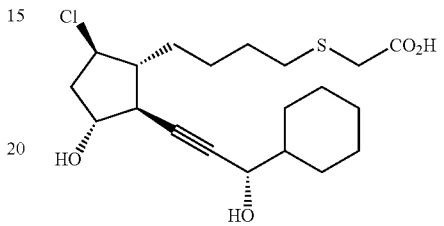

Compound No. 7

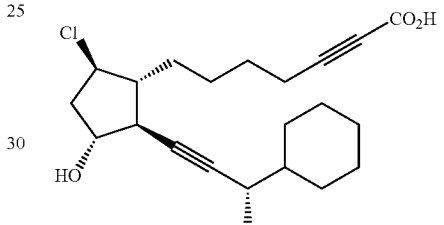

Compound No. 15

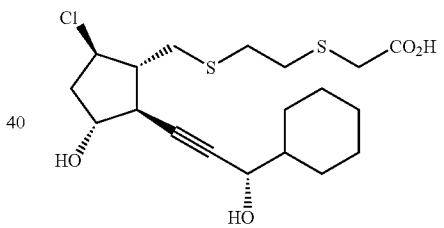

Compound No. 25

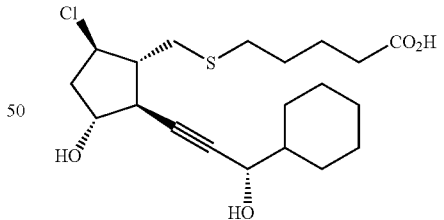

Compound No. 32

| Compound | Concentration (%) | Inhibition rate (%) | Efficacy |
|---|---|---|---|
| EtOH | 100 | 10.2 | NS |
| 6 | 0.0001 | 32.26 | * |
| 7 | 0.000001 | 43.26 | ** |
| 15 | 0.000001 | 34.61 | * |
| 25 | 0.00001 | 21.51 | * |
| 32 | 0.00001 | 41.76 | ** |

*: $P < 0.05$,
**: $P < 0.01$

Test Example 2

Effect on Dermatitis Manifesting NC Mouse Models

By suitably modifying a method known to the skilled artisan (Jpn. J. Pharmacol. 76, 175-183 (1998) Jun Hiroi, et al. Effects of Tacrolimus Hydrate (FK-506) Ointment on Spontaneous Dermatitis in NC/Nga Mice), the following test was conducted in order to confirm the antipruritic effect of compounds of the invention.

(Method)

Animals: Four-week old SPF NC mice (male) were purchased from Japan SLC; right after their arrival, the SPF NC mice were kept together with dermatitis manifesting male NC mice (older than 20 weeks) for 2 weeks under the following conditions so as to induce itch-evoked scratching behavior. A group of mice manifesting dermatitis and another group of mice not manifesting dermatitis, each consisting of four animals, were allowed to cohabit in a sawdust cage (34×17×39 cm) and kept in an animal house set at room temperature (23±3° C.) and at a humidity of 55±15% under illumination for 12 hours (from 7:00 am to 7:00 pm).

After 2-wk cohabitation, the purchased mice were taken out of the cage and transferred into another cage, where a group of 8 animals were kept for about 14 weeks. Immediately before the application of a drug, the mice were reshuffled so that the dermatitis scores would be equal among all cages and then kept, four animals per cage.

Tacrolimus was purchased from Fujisawa Pharmaceutical Co., Ltd. for use in the experiment.

Drug administration: To the dorsal backs of the 20-wk NC mice that were induced to manifest dermatitis as the result of cohabitation with the spontaneous dermatitis manifesting NC mice, 100% ethanol, compound No. 7 (0.01%) dissolved in 100% ethanol or tacrolimus (0.1%) dissolved in 100% ethanol was applied from an Eppendorf pipette in 200-µl doses seven times a week for a period of 4 weeks. The non-treatment group was not given any treatment. Each test group consisted of 8 animals that were observed for any dermatitic symptoms.

Dermatitis score: Dermatitic symptoms were observed and measured once a week.

Four factors, smoothness of fur, loss of hair, bleeding and scab formation, were rated by the following scores: 0, no symptom; 1, mild symptom; 2, moderate symptom; 3, severe symptom (minimum sum, 0; maximum sum, 12).

(Results)

The results of observation of dermatitic symptoms are shown in FIG. 1.

The groups administered with tacrolimus and compound No. 7 showed significant dermatitis score suppressing action compared to the vehicle group.

Test Example 3

Effect on the Spontaneous, Itch-Evoked Scratching Behavior of NC Mice (Experimental)

Figure 2:
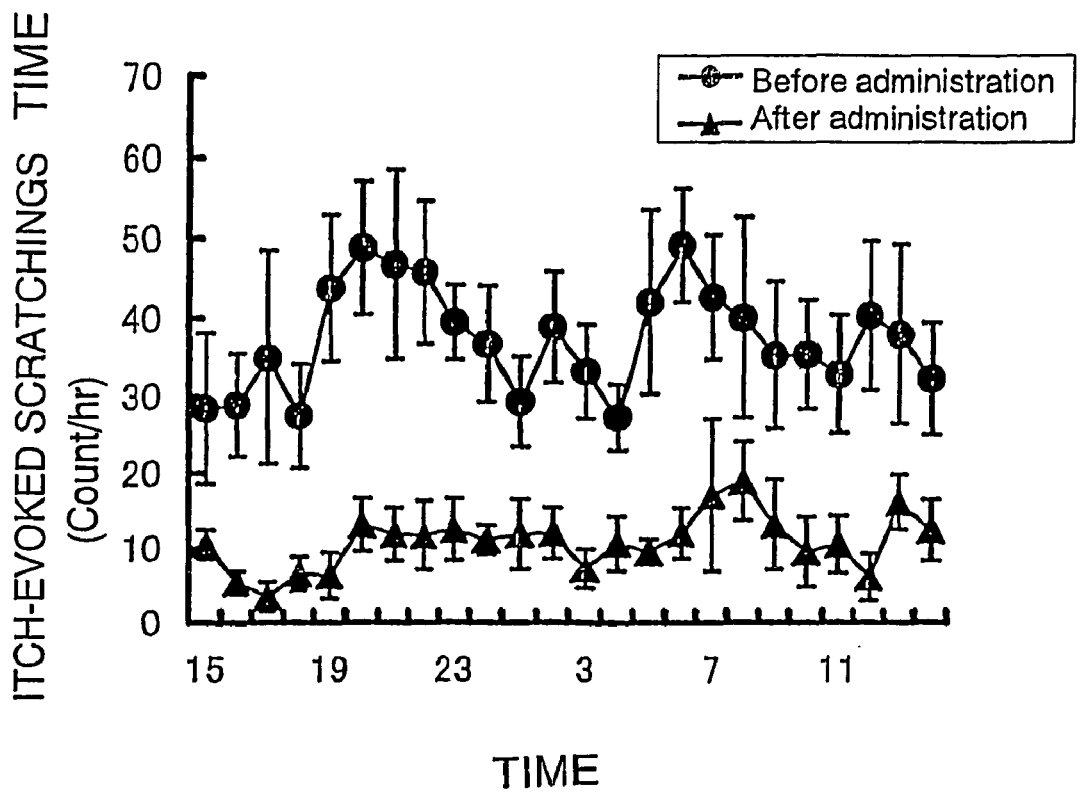
FIG. 2 shows the results of a test for suppressing spontaneous itch-evoked scratching behavior by administering compound No. 3.
Figure 3:
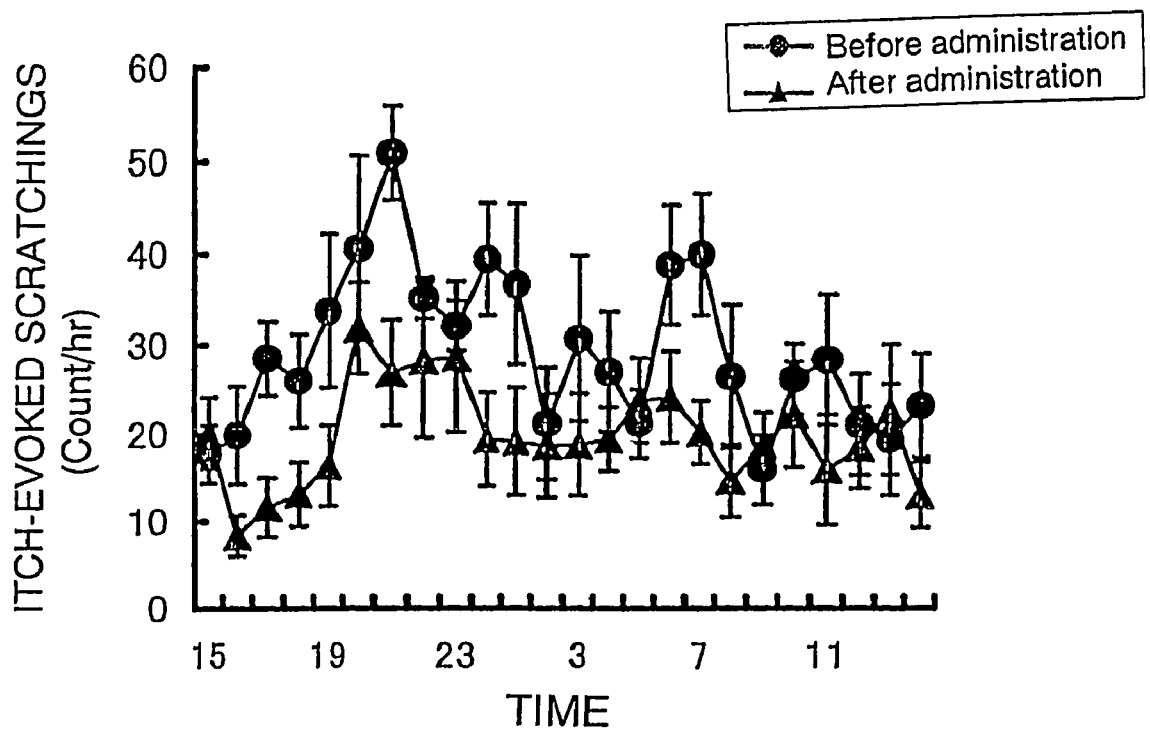
FIG. 3 shows the results of a test for suppressing spontaneous itch-evoked scratching behavior by administering compound No. 11.
Figure 3:
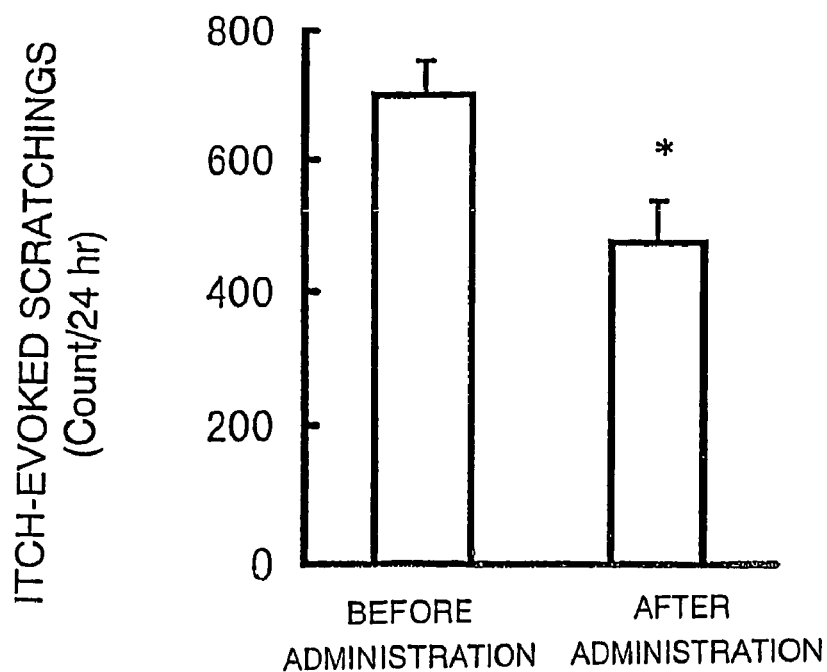
Figure 4:
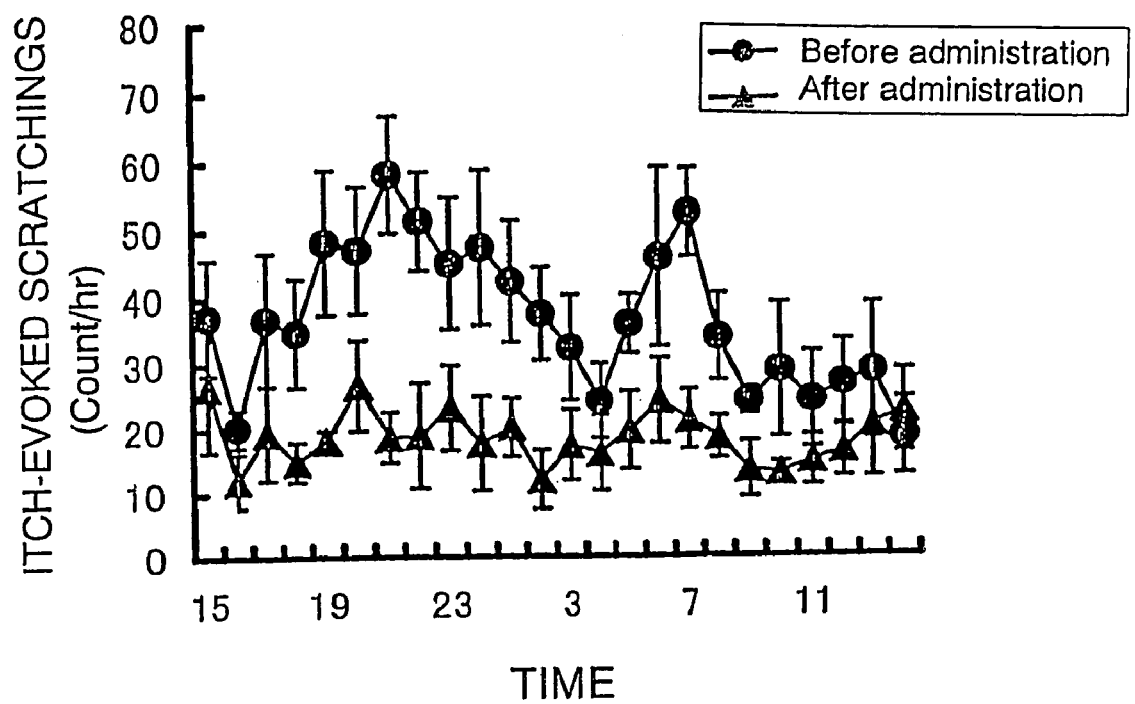
FIG. 4 shows the results of a test for suppressing spontaneous itch-evoked scratching behavior by administering compound No. 12.

About 20-week old NC/Nga mice each weighing about 30 g and manifesting atopic dermatitis were purchased from SLC and subjected to the following experiment. A magnet was buried in both hind paws of each mouse and by detecting its magnetism, the movement of the paws was measured with an itch measuring system (product of Neuroscience). Among the scratching actions, those lasting 1.5 seconds or longer were considered itch-evoked and their number was counted continuously. Since the itch-evoked scratching behavior had a diurnal rhythm, the diurnal rhythm of each individual animal was measured for 24 hours of the day before test and only after that, compound No. 3 (0.1%), compound No. 11 (0.1%) or compound No. 12 (0.1%) dissolved in 100% ethanol was applied to the dorsal skin in a dose of 0.2 ml/mouse. The subsequent 24-hr itch-evoked scratching behavior was measured and the number of itch-evoked scratchings after drug administration was compared with the initial count. The structures of the test compounds are shown below and the changes with time in the spontaneous itch-evoked scratching counts, as well as the 24-hr total spontaneous itch-evoked scratching counts before and after administration of a compound are shown in FIGS. 2-4.

For significance testing, the itch-evoked scratching counts that were obtained before and after drug application from individual animals in each group treated with a specific concentration of drug were processed by a paired t-test.

Compound No. 3

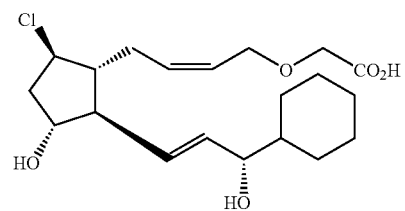

Compound No. 11

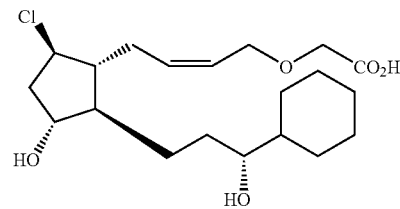

Compound No. 12

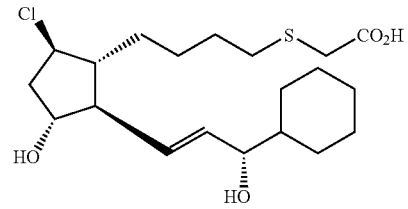

Reference Example 1

Changes in the PGs Contents in the Mouse Skin Tissue

NC/Nga male mice (5, 10, 15 and 20 weeks old) were used in the test. For correct measurement of endogenous prostaglandin (PG), indomethacin (10 mg/kg) was i.v. injected to suppress any additional endogenous PG production and 5 minutes later, the dorsal skin was sampled with a pair of scissors. A slice of skin was transferred into a tube and after adding 1 mL of PBS (containing 100 µM of indomethacin), the tissue was comminuted with a POLYTRON homogenizer. After adding 4 mL of acetone and subsequent standing for 5 minutes, the mixture was centrifuged at 3000 rpm for 10 minutes. After recovering the supernatant, the solvent was evaporated and the residue was redissolved in an ELISA buffer; the contents of various PGs ($PGD_2$, $PGE_2$, $PGF_{2\alpha}$, and 6-keto-$PGF_{1\alpha}$) were measured with an ELISA kit (Cayman Chemical, R&D Systems) to determine their respective contents in 1 mg of the skin.

Figure 5:
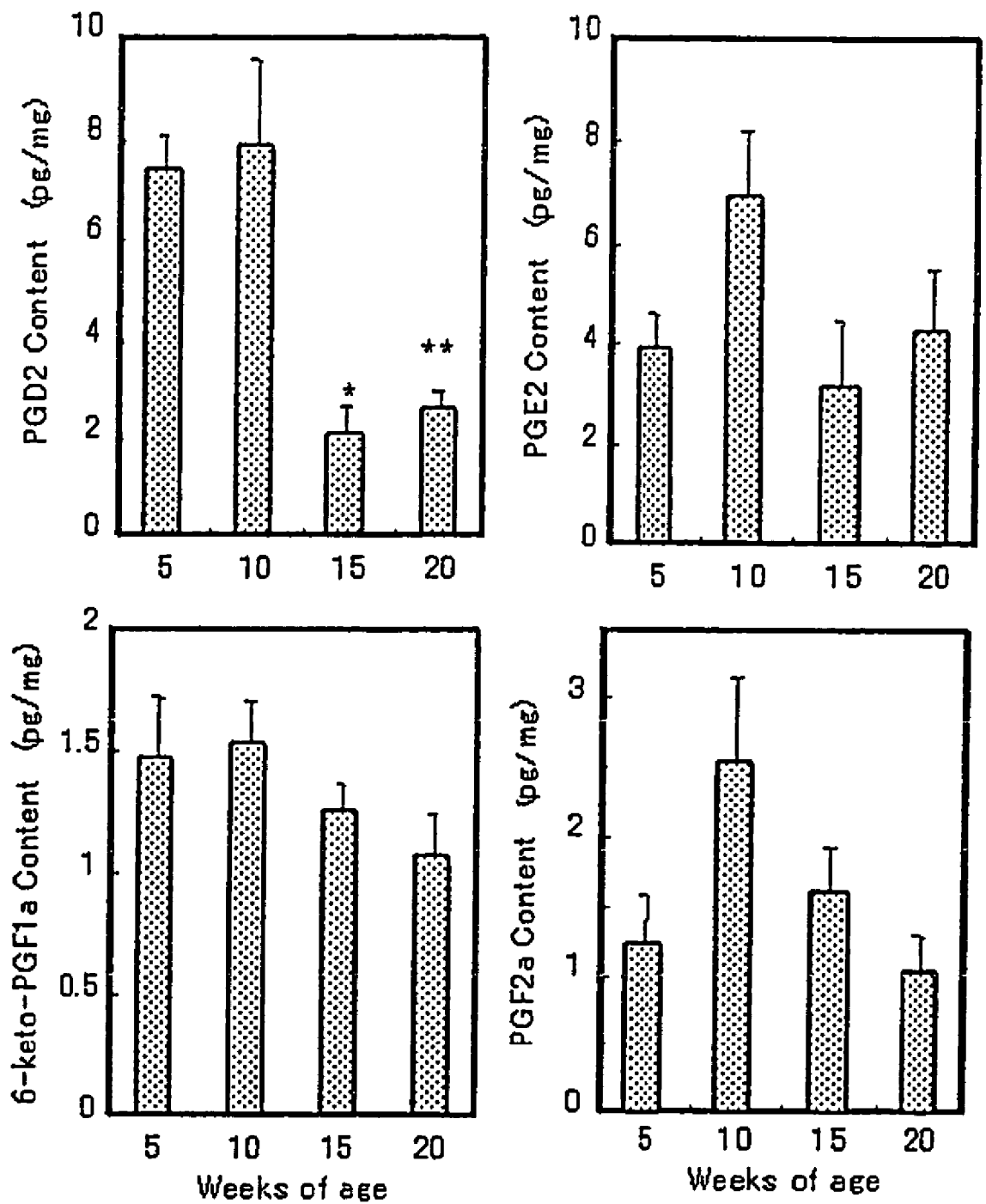
FIG. 5 is a set of graphs showing the changes with aging in the contents of various prostaglandins in the mouse skin, with each vertical axis plotting the contents of various prostaglandins and each horizontal axis plotting the age of each mouse in weeks; * and ** mean significant differences at p<0.05 and p<0.01 from the value in the 5-week-old mice.

The results are shown in FIG. 5.

As is clear from FIG. 5, the NC/Nga mice got their $PGD_2$ content in the skin to decrease with aging.

Test Example 4

(A) Using the active ingredient of the present invention (compound No. 7) and $PGD_2$ as a control for comparison, prostaglandin D receptor binding selectivity was determined with reference to the platelet aggregation suppressing action as the prostaglandin D receptor agonist action.

1. Human Platelet Aggregation Suppressing Action

Suppression of ADP-Induced Aggregation of Human Platelets

The test was performed on purchased platelet-rich plasma (PRP) ($6 \times 10^8$ platelets/mL) and platelet aggregation was measured based on the Born method (Nature, vol. 194, p. 927, 1962). To 100 µL of PRP, 5 µL of a 1 nM-3 µM test drug solution in ethanol was added and the mixture was incubated at 37° C. for 1 minute with stirring at 1000 rpm. To the resulting mixture, 5 µL of an aggregation inducer [ADP (3 µM)] was added to induce platelet aggregation and a maximum percent aggregation (a maximum change in light transmittance that occurred within 5 minutes after the induction of platelet aggregation) was determined by an aggregometer. The percent suppression of aggregation by each test drug was calculated from the maximum percent aggregation by the test drug as relative to the maximum percent aggregation by ethanol instead of the test drug solution and $IC_{50}$ values were determined from the constructed dose-response curve. The results were: compound No. 7 had an $IC_{50}$ of 4.27 nM and $PGD_2$ had an $IC_{50}$ of 11 nM.

2. Guinea Pig Platelet Aggregation Suppressing Action

Blood Sampling and Preparing of Platelet-Rich Plasma (PRP) and Platelet-Poor Plasma (PPP)

Ten-week-old Hartley male guinea pigs were anesthetized with pentobarbital (30 mg/kg, i.p. injected) and a total of 20 mL of blood was sampled into a syringe containing 2.0 mL of 3.8% sodium citrate. The blood was immediately centrifuged at 900 rpm for 10 minutes at 20° C. to recover the supernatant PRP. By further centrifugation at 3000 rpm for 10 minutes at 20° C., the supernatant PPP was recovered. The platelet count of PRP was diluted with PPP to $30 \times 10^4$ platelets/µL for subsequent use.

Suppression of ADP Induced Aggregation of Guinea Pig Platelets

For platelet aggregation measurement, a platelet aggregation measuring instrument (PAM-8C) was employed. To 274 µL of PRP, 1 µL of a 0.287-95.7 nM test drug solution in ethanol was added and the mixture was incubated at 37° C. for 3 minutes with stirring at 1000 rpm. After the incubation, 25 µL of ADP (3 µM) was added to induce platelet aggregation and a maximum percent aggregation for 5 minutes was measured.

The percent suppression of aggregation by each test drug was calculated from the maximum percent aggregation by the test drug as relative to the maximum percent aggregation by ethanol instead of the test drug solution and $IC_{50}$ values were determined from the constructed dose-response curve.

The results were: compound No. 7 had an $IC_{50}$ of 6.2±2.3 nM and $PGD_2$ had an $IC_{50}$ of 54.3±23.0 nM.

(B) In order to confirm that the action demonstrated in (A) of the active ingredient of the present invention and $PGD_2$ in suppressing platelet aggregation is the prostaglandin D receptor agonistic action, a test was conducted to see whether the platelet aggregation suppressing action of compound No. 7 and $PGD_2$ would be antagonized by a prostaglandin D receptor selective antagonist.

Test Drug:

The prostaglandin D receptor selective antagonist used in the test was ((+/−)-3-benzyl-5-(6-carboxyhexyl)-1-(2-cyclohexyl-2-hydroxyethylamino)-hydantoin) (hereunder designated BW A868C) (Sigma-Aldrich Japan K.K.)

BW A868C was diluted with ethanol to final concentrations of 0.03 µmol/L, 0.1 µmol/L, 0.3 µmol/L, 1 µmol/L, 3 µmol/L and 10 µmol/L.

Compound No. 7 and $PGD_2$ were diluted with ethanol to 287 nmol/L and 300 nmol/L, respectively, for subsequent use.

The negative control was ethanol.

Preparing of Platelets:

Blood was taken from the cubital veins of human healthy males and sampled into a tube containing 3.13% sodium citrate. The blood sample was centrifuged at 1,000 rpm for 10 minutes at 20° C. to separate the supernatant (PRP, or platelet-rich plasma) and the residue was further centrifuged at 3,000 rpm for 10 minutes at 20° C. to separate the supernatant (PPP, or platelet-poor plasma). The platelet count of PRP was appropriately diluted with PPP to $30 \times 10^4$ platelets/µL for subsequent use.

Measurement of Platelet Aggregation

Platelet aggregation was measured with a platelet aggregation measuring instrument (PAM-8C; MC MEDICAL Co., LTD.) by the Born method (Nature, vol. 194, p. 927, 1962). A portion (273 µL) of PRP (for the BW A868C groups, 1 µL of BW A868C was added at varying concentrations) was preincubated at 37° C. for 3 minutes with stirring at 1,000 rpm. After the preincubation, 1 µL of ethanol or a test substance (compound No. 7: final concentration at 95.7 nmol/L; $PGD_2$: final concentration at 1000 nmol/L) was added and the mixture was incubated at 37° C. for 3 minutes with stirring at 1000 rpm. After the incubation, 25 µL of ADP (final concentration at 3 µmol/L) was added to induce platelet aggregation and a maximum percent aggregation for 5 minutes was measured.

Figure 6:
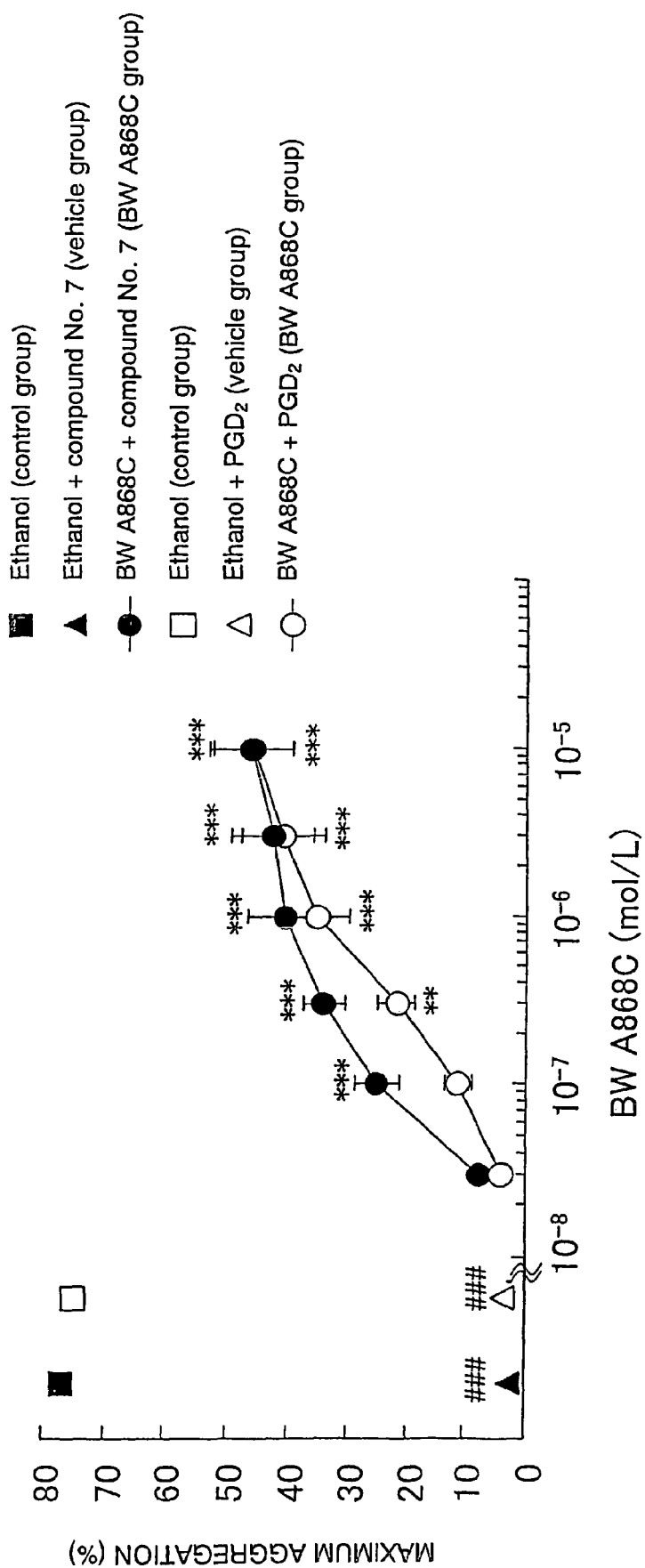
FIG. 6 is a graph showing the suppressive action of compound No. 7 and $PGD_2$ on ADP-induced human platelet aggregation and the antagonistic action of BW A868C, with each value representing the mean±standard error for 6 cases; ### means a significant difference at p<0.001 (paired t-test) from the value in the control group;  and * mean significant differences at p<0.01 and p<0.001 from the value in the vehicle group (Dunnett test of two-dimensional layout).

The results are shown in FIG. 6.

Compound No. 7 and $PGD_2$ showed a significant platelet aggregation suppressing action as compared with their respective control groups (ethanol).

The platelet aggregation suppressing action of compound No. 7 was antagonized by the increasing concentration of BW A868C and significant antagonism was observed at 0.1 µmol/L or more of BW A868C. The platelet aggregation suppressing action of $PGD_2$ was also antagonized by the increasing concentration of BW A868C and significant antagonism was observed at 0.3 µmol/L or more of BW A868C.

These results clearly show that the active ingredient of the present invention has a prostaglandin D receptor selective agonistic action.

(C) The effect of the active ingredient of the present invention (compound No. 7) on a thromboxane (TP) receptor was measured as compared with the thromboxane agonist U44069 as a positive control drug.

Human TP Antagonistic Action

The antagonistic action of the test drug on the [$^3$H] SQ29548 binding to human washed platelets was investigated on the basis of a documented method (J. Pharmacol. Exp. Ther., vol. 245, pp. 786-792, 1988).

As it turned out, compound No. 7 showed 28% binding inhibition at a concentration of 10 μM and 7% inhibition at 1 μM. On the other hand, U44069 as the positive control drug had an $IC_{50}$ of 2.4 μM.

As is clear from these results, the active ingredient of the present invention showed high selectivity for the prostaglandin D receptor.

Since the active ingredient of the present invention had weak action on the thromboxane (TP) receptor, it was found to cause neither potent vasoconstriction nor platelet aggregation which are two side effects of the thromboxane (TP) receptor agonist.

Test Example 5

Effect on the Mouse Skin's Barrier Function
(Treatment Test)

Six-week-old BALB/c male mice in groups of eight were shaven in a rostral dorsolateral area of 4 cm$^2$ (2 cm×2 cm) with electric clippers and the shaven area was covered for 60 seconds with an absorbent cotton (2 cm×2 cm) impregnated with a 1:1 liquid mixture of acetone and diethyl ether. This treatment for destroying the skin's barrier function was performed for 3 consecutive days on once-a-day basis. Starting on the day next to completion of the treatment for barrier destruction at day 3, a solvent (ethanol, 100 μL) or a drug dissolved in the solvent (compound No. 7, $PGD_2$, $PGF_{2\alpha}$, or $PGE_1$, all being at 0.01% in an amount of 100 μL) was applied to the barrier destroyed site for 2 days on once-a-day basis. On the day next to the second application of the solvent or drug, the transepidermal water loss (TEWL) at the same site was measured with Tewameter (TM210 of Courage & Khazawa, Germany) to evaluate the drug's action. The results are shown in FIG. 7.

Figure 7:
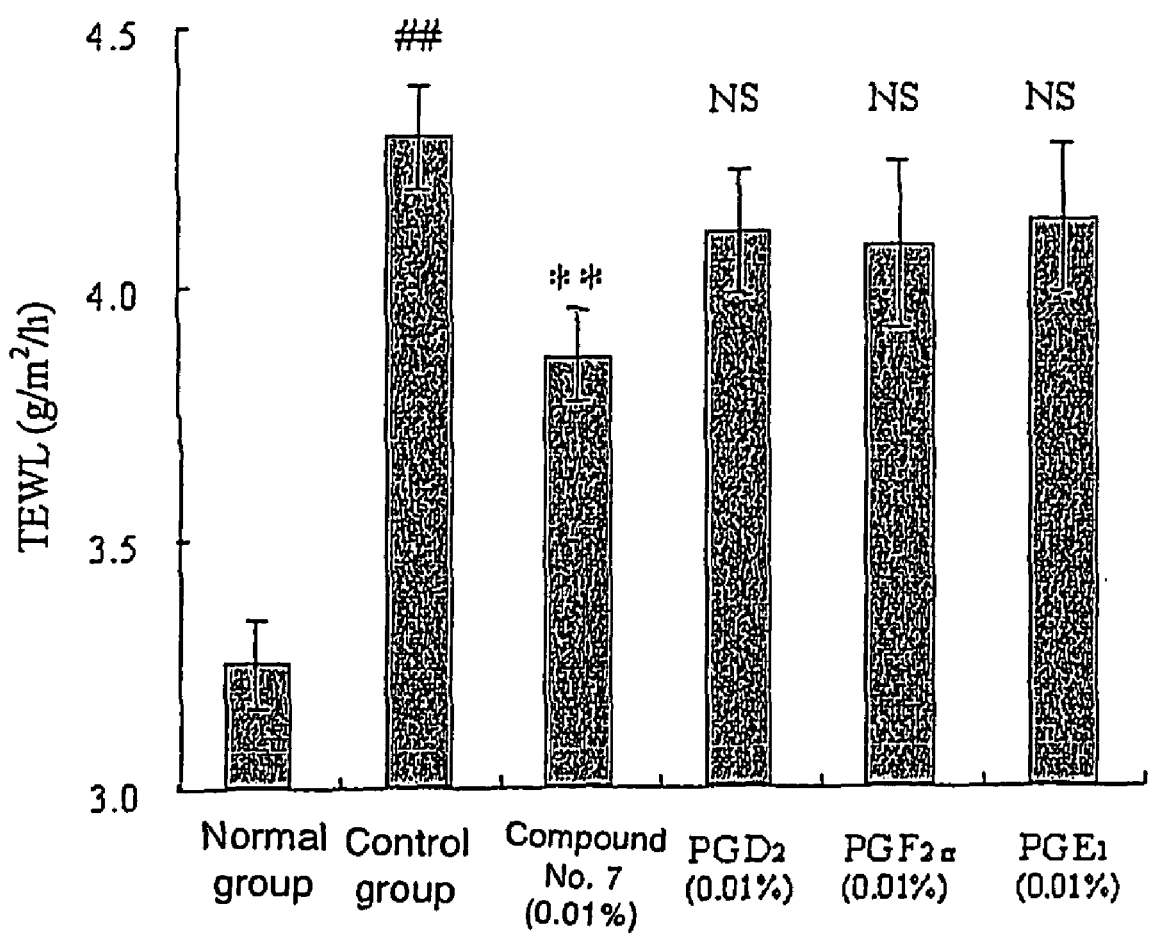
FIG. 7 is a graph showing the transepidermal water loss from mice coated with various drugs, with the vertical axis plotting the transepidermal water loss and the horizontal axis plotting the type of drug; ## means a significant difference at p<0.01 from the normal group; * and ** mean significant differences at p<0.05 and p<0.01 from the control group.

As is clear from FIG. 7, the solvent-applied control group which was subjected to barrier destruction saw a significant increase in TEWL compared to the normal group. The group coated with compound No. 7 saw a significant decrease in TEWL compared to the solvent-applied control group. On the other hand, the $PGD_2$-, $PGF_{2\alpha}$- and $PGE_1$-applied groups had no significant difference from the control group.

These results show that the active ingredient of the present invention has the action of promoting the healing of a destroyed skin barrier.

Test Example 6

Effect on the Mouse Skin's Barrier Function
(Preventive Test)

Six-week-old BALB/c male mice in groups of six were shaven in a rostral dorsolateral area of 4 cm$^2$ (2 cm×2 cm) with electric clippers and kept in the same cage as NC/Nga mice that had developed dermatitis. From the day next to the start of cohabitation, a solvent (ethanol, 100 μL) or a drug dissolved in the solvent (compound No. 7, $PGD_2$, $PGF_{2\alpha}$, or $PGE_1$, all being at 0.01% in an amount of 100 μL) was applied to the shaven site for 7 days on once-a-day basis.

On the day next to the seventh application of the solvent or drug, the transepidermal water loss (TEWL) at the same site was measured with Tewameter (TM210 of Courage & Khazawa, Germany) to evaluate the drug's action, with the solvent-applied group being used as the control group. The results are shown in FIG. 8.

Figure 8:
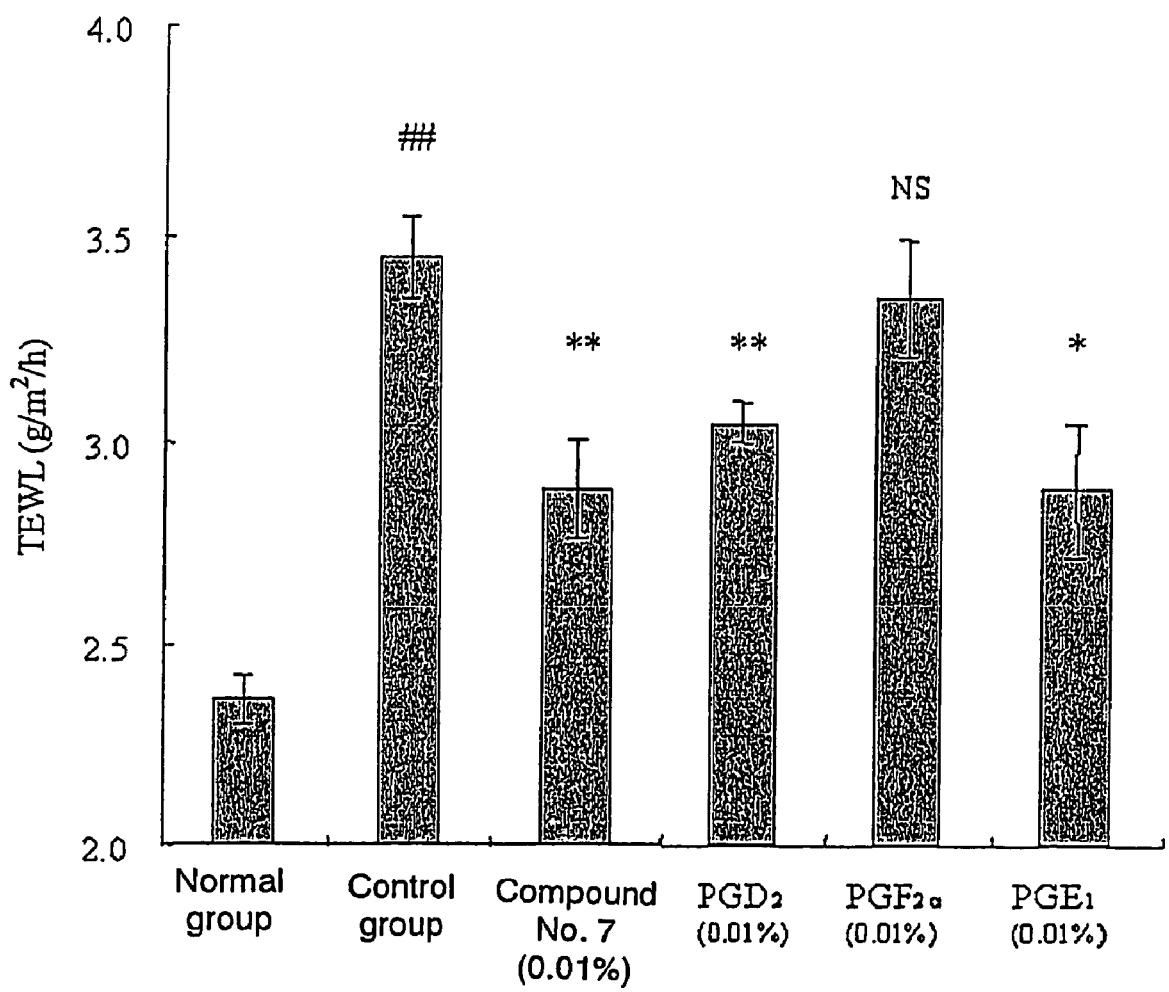
FIG. 8 is a graph showing the transepidermal water loss from mice coated with various drugs, with the vertical axis plotting the transepidermal water loss and the horizontal axis plotting the type of drug; ## means a significant difference at p<0.01 from the normal group; * and ** mean significant differences at p<0.05 and p<0.01 from the control group.

As is clear from FIG. 8, the control group saw a significant increase in TEWL compared to the normal group. The group coated with compound No. 7, $PGD_2$ or $PGE_1$ saw a significant decrease in TEWL compared to the control group. On the other hand, the $PGF_{2\alpha}$-applied group had no significant difference from the control group.

These results show that the active ingredient of the present invention has the action of preventing damage to the skin's barrier and that, therefore, the active ingredient of the present invention has a preventive action on a damaged skin barrier condition such as xerosis.

Reference Example 2

Senile Xeroderma Model

A senile xeroderma model was established by the following method which could verify that the mouse also gets TEWL (an index of skin's barrier function) to increase with aging.

Experimental

BALB/c male mice (eight in each group) at ages of 6, 12, 24 and 50 weeks were shaven in a rostral dorsolateral area of 4 cm$^2$ (2 cm×2 cm) with electric clippers and TEWL (an index of skin's barrier function) was measured with Tewameter (TM210 of Courage & Khazawa, Germany). The results are shown in FIG. 9.

Test Results

Figure 9:
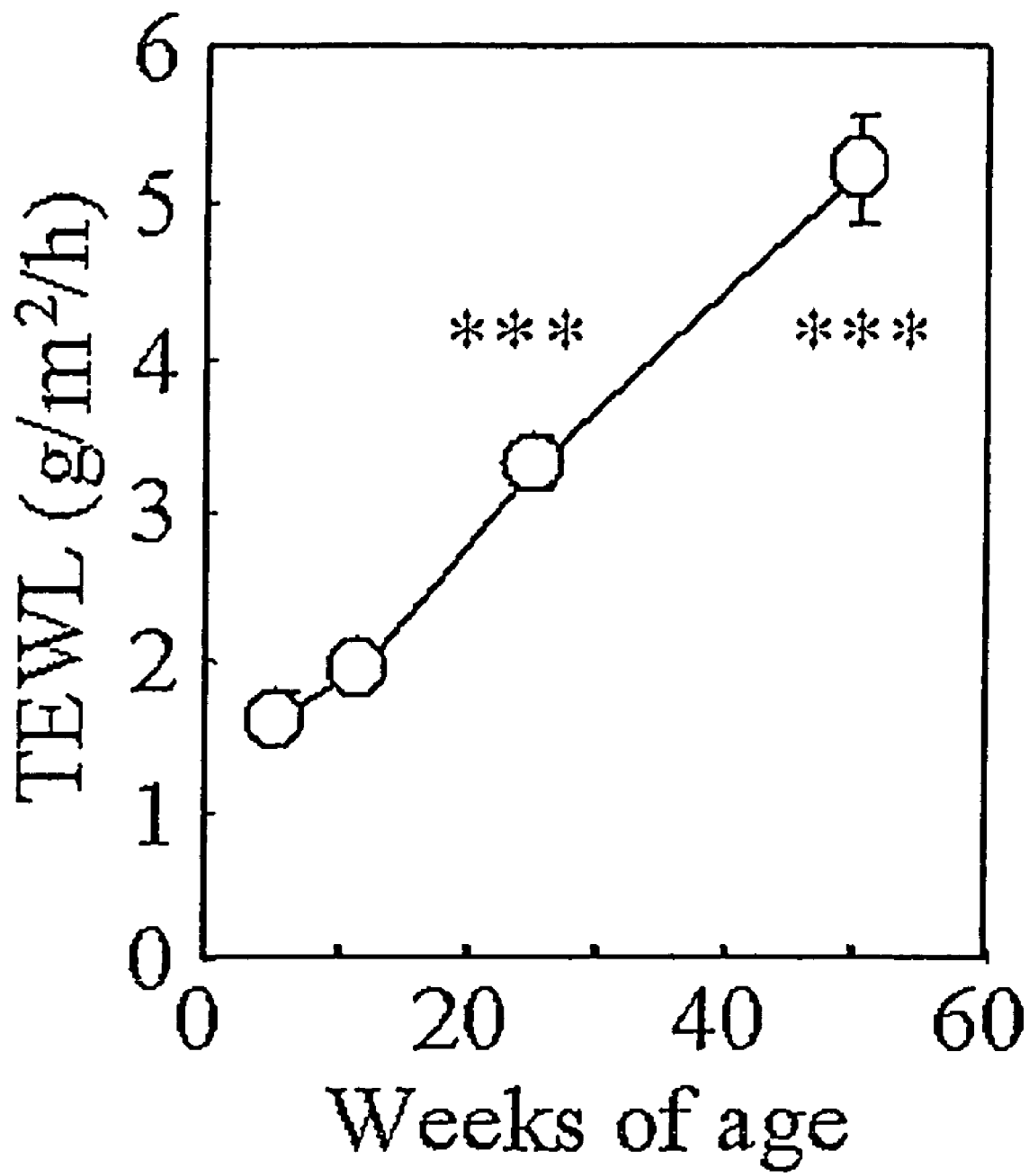
FIG. 9 is a graph showing the changes with aging in the transepidermal water loss from mice coated with various drugs, with the vertical axis plotting the transepidermal water loss and the horizontal axis plotting the age of mice; *** means a significant difference at p<0.001 from the 6-week mice.

As is clear from FIG. 9, TEWL or an index of skin's barrier increased in mice with aging, providing a verification of dermal disorder due to the destroyed skin function.

Test Example 7

Effect on Aged Mouse Skin's Barrier Function
(Treatment Test)

Fifty-week-old BALB/c male mice (eight in each group) were shaven in a rostral dorsolateral area of 4 cm$^2$ (2 cm×2 cm) with electric clippers. Starting on the next day, a solvent (ethanol, 200 μL) or a drug dissolved in the solvent (compound No. 7 or $PGD_2$, each being at 0.0001% in an amount of 200 μL) was applied to the shaven site for 3 days on once-a-day basis.

On the day next to the third application of the solvent or drug, TEWL at the same site was measured with Tewameter (TM210 of Courage & Khazawa, Germany) to evaluate the drug's action. The results are shown in FIG. 10.

Figure 10:
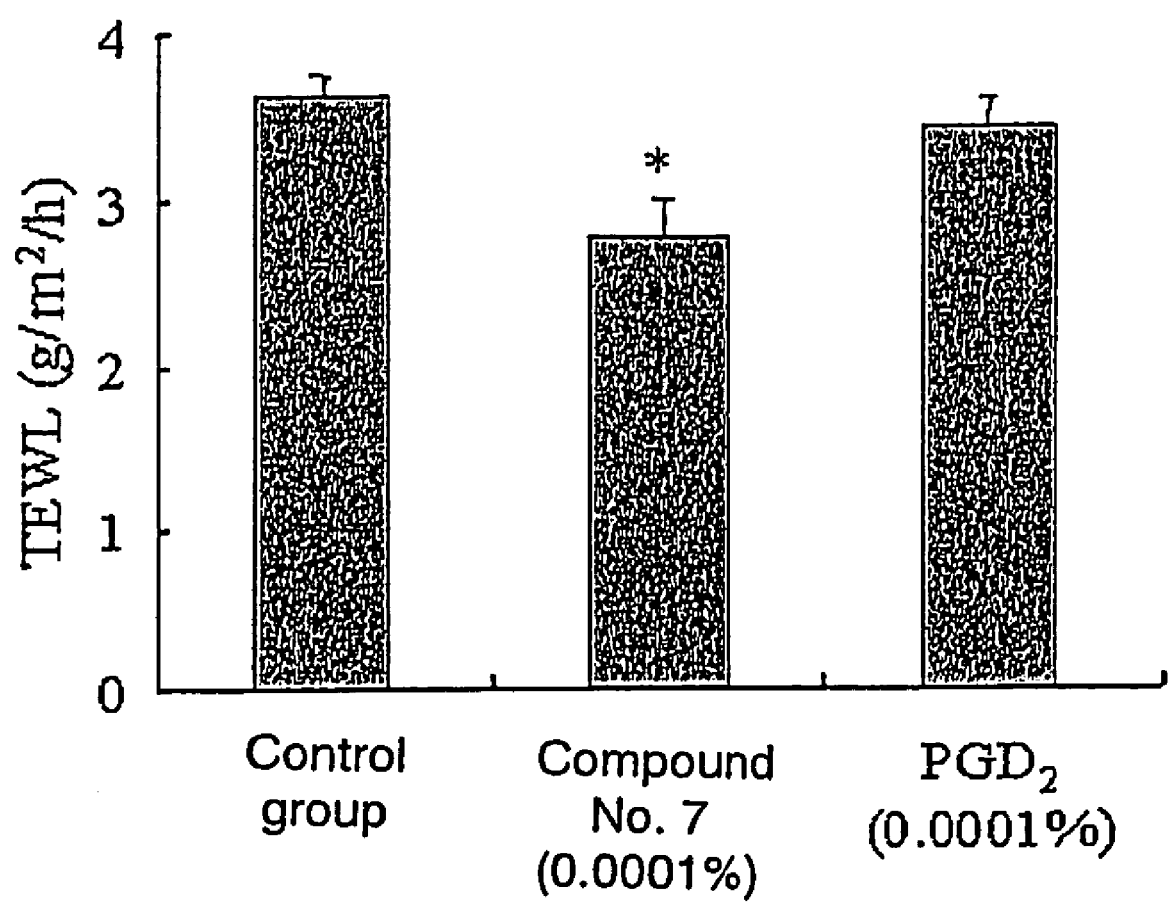
FIG. 10 is a graph showing the transepidermal water loss from mice coated with various drugs, with the vertical axis plotting the transepidermal water loss and the horizontal axis plotting the type of drug; * means a significant difference at p<0.05 from the control group.

As is clear from FIG. 10, the group coated with compound No. 7 saw a significant decrease in TEWL compared to the control group. On the other hand, the $PGD_2$-applied group had no significant difference from the control group.

These results show that the active ingredient of the present invention has the action of promoting restoration of the skin barrier and that, therefore, the active ingredient of the present invention has a treatment action on a damaged skin barrier condition such as senile xeroderma.

INDUSTRIAL APPLICABILITY

Having enabled reducing the frequency of itch-evoked scratching behavior that induces dermatitis, the present invention successfully provides pharmaceutical preparations that can prevent or ameliorate various cases of dermatitis including atopic dermatitis, atopic conjunctivitis, scabies, urticaria and xerosis.

In particular, the present invention has enabled providing highly safe and efficacious drugs for preventing or treating xerosis, thereby making it possible to prevent or treat dermatitis resulting from xerosis.

The invention claimed is:

1. A method for treating xerosis which comprises applying a prostaglandin D receptor selective agonist to a mammal, wherein the prostaglandin D receptor selective agonist is a prostaglandin derivative represented by formula

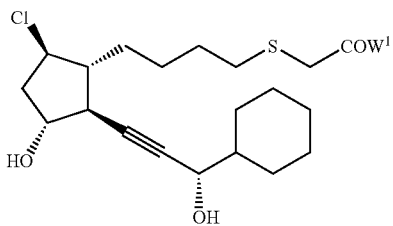

[B]

wherein,
$W^1$ is a hydroxyl group or a $C_{1-10}$ alkyloxy group,
a pharmaceutically acceptable salt thereof or a hydrate thereof.

2. The method according to claim 1, wherein the prostaglandin D receptor selective agonist is a compound represented by formula [B]
wherein $W^1$ is a hydroxyl group or a methoxyl group,
a pharmaceutically acceptable salt thereof or a hydrate thereof.

3. The method according to claim 1, wherein the prostaglandin D receptor selective agonist is a compound represented by formula

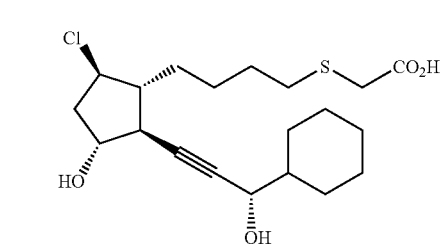

a pharmaceutically acceptable salt thereof or a hydrate thereof.

4. The method according to claim 1, wherein the xerosis is senile xeroderma.

5. The method according to claim 1, wherein the xerosis is treated by decreasing transepidermal water loss.

* * * * *

UNITED STATES PATENT AND TRADEMARK OFFICE
CERTIFICATE OF CORRECTION

PATENT NO. : 7,737,182 B2  Page 1 of 1
APPLICATION NO. : 11/049641
DATED : June 15, 2010
INVENTOR(S) : Iwao Arai et al.

It is certified that error appears in the above-identified patent and that said Letters Patent is hereby corrected as shown below:

Title Page, Item (63) Related U.S. Appl. Data should read
--(63) Continuation-in-part of application No. 10/493,693, filed April 27, 2004, ~~as application No.~~ which is a 371 of PCT/JP03/10051 filed Aug. 7, 2003 ~~on Aug. 7, 2001~~.--

Signed and Sealed this

Fourteenth Day of December, 2010

David J. Kappos
*Director of the United States Patent and Trademark Office*